United States Patent [19]
Broadway et al.

[11] Patent Number: 6,069,299
[45] Date of Patent: May 30, 2000

[54] FUNGUS AND INSECT CONTROL WITH CHITINOLYTIC ENZYMES

[75] Inventors: Roxanne M. Broadway, Phelps; Gary E. Harman, Geneva, both of N.Y.

[73] Assignee: Cornell Research Foundation, Inc., Ithaca, N.Y.

[21] Appl. No.: 09/025,691

[22] Filed: Feb. 18, 1998

[51] Int. Cl.[7] .............................. C12N 5/04; C12N 15/31; C12N 15/56; C12N 15/82; A01H 5/00

[52] U.S. Cl. ........................ 800/279; 435/69.1; 435/200; 435/320.1; 435/418; 435/419; 435/468; 435/252.3; 536/23.7; 800/288; 800/298; 800/302; 800/306; 800/307; 800/308; 800/309; 800/310; 800/312; 800/313; 800/314; 800/320; 800/321; 800/323

[58] Field of Search .............................. 435/320.1, 69.1, 435/418, 419, 468, 410, 252.3, 200; 424/93.2; 800/278, 279, 288, 295, 298, 301, 302, 317, 320, 306, 307–310, 312–313, 314, 321, 323; 536/23.7

[56] References Cited

U.S. PATENT DOCUMENTS

| | | | |
|---|---|---|---|
| 4,751,081 | 6/1988 | Suslow et al. | 424/93 |
| 4,996,157 | 2/1991 | Smith et al. | 435/254 |
| 5,165,928 | 11/1992 | Smith et al. | 424/93 |
| 5,173,419 | 12/1992 | Harman et al. | 435/209 |
| 5,260,213 | 11/1993 | Harman et al. | 435/254.6 |
| 5,288,634 | 2/1994 | Harman et al. | 435/254.1 |
| 5,326,561 | 7/1994 | Harman et al. | 424/94.61 |
| 5,360,608 | 11/1994 | Harman et al. | 424/94.61 |
| 5,433,947 | 7/1995 | Harman et al. | 424/94.61 |
| 5,474,926 | 12/1995 | Harman et al. | 435/200 |
| 5,633,450 | 5/1997 | Suslow et al. | 800/284 |

FOREIGN PATENT DOCUMENTS

| | | | |
|---|---|---|---|
| 0 401 560 A1 | 12/1990 | European Pat. Off. | C12N 1/20 |
| 41 17 026 A1 | 11/1992 | Germany | C12N 15/79 |
| WO 97/08944 | 3/1997 | WIPO | A01H 5/00 |
| WO 97/32973 | 9/1997 | WIPO | C12N 9/24 |

OTHER PUBLICATIONS

Lorito, M. Chitinolytic Enzymes and Their Genes, In Trichoderma and Gliocladium, vol. II, Haren and Kubicek, Eds., pp. 73–75, 1998.

Lorito et al, MPMI, vol. 9, pp. 206–213, 1996.

Neuhaus et al, Plant Mol. Biol., vol. 16, pp. 141–151, 1991.

Kramer et al, In Transgenic Plants for the Control of Insect Pests, N. Carrozzi & M. Koziel, eds., Washington, D.C., pp. 185–193, 1996.

Wang et al, Insect Biochem. Molec. Biol., vol. 26., pp. 1055–1064, 1996.

Zhu et al, J. Biochem., vol. 112, pp.163–167, 1992.

Monreal et al., "The Chitinase of *Serratia marcescens*," *Canadian Journal of Microbiology*, 15:689–696 (1969).

Regev et al., "Synergistic Activity of a *Bacillus thuringiensis* δ–Endotoxin and a Bacterial Endochitinase Against *Spodoptera littoralis* Larvae," *Applied and Environmental Microbiology*, 62(10):3581–3586.

Park et al., "Production and Some Properties of Chitinolytic Enzymes by Antagonistic Bacteria," *Korean J. Plant Pathol.* 11(3):258–264 (1995).

Tsujibo et al., "Cloning and Sequence Analysis of the Gene Encoding a Thermostable Chitinase from *Streptomyces thermoviolaceus* OPC–520," *Gene* 134:113–117 (1993).

Pleban et al., "Chitinolytic Activity of an Endophytic Strain of *Bacillus cereus*," *Letters in Applied Microbiology* 25(4):284–288 (1997).

Bolar et al., "Endochitinase—Transgenic McIntosh Apple Lines Have Increased Resistance to Scab," *Phytopathology* 87(6):S10 (1997) (abstract).

Broadway et al., "Novel Chitinolytic Enzymes with Biological Activity Against Herbivorous Insects," *J. Chem. Ecol.* 24(6):985–998 (1998).

Wong et al., "Chitinase–Transgenic Lines of 'Royal Gala' Apple Showing Enhanced Resistance to Apple Scab," *ACTA Hortic*, 484:595–599 (1996).

Xue, B., et al., "Development of Transgenic Tomato Expressing a High Level of Resistance to Cucumber Mosaic Virus Strains of Subgroups I and II," *Plant Disease* 78(11):1038–41 (1994).

Pang, S., et al., "Different Mechanisms Protect Transgenic Tobacco Against Tomato Spotted Wilt and Impatiens Necrotic Spot *Tospoviruses*," *Bio/Technology* 11:819–24 (1993).

Broadway, R.M., et al., "Partial Characterization of Chitinolytic Enzymes from *Streptomyces albidoflavus*," *Applied Microbiology* 20:271–76 (1995).

*Primary Examiner*—David T. Fox
*Assistant Examiner*—Ashwin D. Mehta
*Attorney, Agent, or Firm*—Nixon Peabody LLP

[57] ABSTRACT

The present invention relates to chitinolytic enzymes which have chitinolytic activity under alkaline conditions as well as DNA molecules encoding these enzymes and expression systems, host cells, and transgenic plants and plant seeds transformed with such DNA molecules. A chitinolytic enzyme can be applied to a plant or plant seed under conditions effective to control insects and/or fungi on the plant or plants produced from the plant seed. Alternatively, transgenic plants or transgenic plant seeds transformed with a DNA molecule encoding a chitinolytic enzyme can be provided and the transgenic plants or plants resulting from the transgenic plant seeds are grown under conditions effective to control insects and/or fungi.

48 Claims, 14 Drawing Sheets

FUNGUS AND INSECT CONTROL WITH CHITINOLYTIC ENZYMES

The present invention was developed with support under USDA/NRI Grant No. 95-37302-1904. The U.S. Government may have certain rights.

FIELD OF THE INVENTION

The present invention relates to chitinolytic enzymes which are active against insects under alkaline conditions.

BACKGROUND OF THE INVENTION

The introduction of synthetic organic pesticides following World War II brought inestimable benefits to humanity and agricultural economic profitability. Application of broad-spectrum pesticides is the primary method used for controlling fungal and insect pests. For example, the widescale deployment of DDT resulted in the complete riddance, from entire countries, of serious public pests such as malaria mosquitoes. However, there were warnings about the hazard of unilateral approaches to pest control.

The development of new pesticides and the increasing amounts of pesticides used for pest control are closely correlated with the development of pest resistance to chemicals. The number of pesticide resistant species has greatly increased since the adoption of DDT in 1948. As a result, by the 1980s, the number of reports of pesticide resistance for arthropod pests was listed as 281, for plant pathogens 67, and for weeds 17. These numbers have steadily increased to the present day. Thus, the need for biological control agents, especially those with broadbase activity is especially important.

One approach that is gaining significant attention is the use of agricultural cultivars that are resistant to pests. These cultivars can be developed by the transgenic introduction of target specific natural resistance factors. However, to enhance host-plant resistance, it is necessary first to identify and to characterize target-specific factors that will significantly reduce the population(s) of herbivorous insect(s).

Only a limited number of natural products have been characterized and identified as effective defensive agents against herbivorous insects, few of these are proteins (e.g., proteinase inhibitors, arcelin, alpha-amylase inhibitors, lectins, endotoxin from *Bacillus thuringiensis*, and lipoxygenases), and even fewer are target specific (Duffey, et al., "Plant Enzymes in Resistance to Insects," In J. R. Whitaker and P. E. Sonnet (eds.), *Biocatalysis in Agricultural Biotechnology*, American Chemical Society, Washington, D.C. (1989); Gill, et al., "The Mode of Action of *Bacillus thuringiensis* Endotoxins," *Ann. Rev. Entomol.*, 37:615–36 (1992); Hedin, P. A., "Plant Resistance to Insects," American Chemical Society, Washington, D.C., p. 375 (1983); Rosenthal, et al., "Herbivores—Their Interaction with Secondary Plant Metabolites," Academic Press, New York, p. 718 (1979). Identification and characterization of proteins as resistance factor(s) enables the isolation of gene(s) that encode(s) these proteins. These genes can be transgenically inserted into agricultural crops, which may enhance the resistance of these crops against herbivorous insects without altering desirable characteristics of the cultivar(s) (Fraley, et al., "Genetic Improvements of Agriculturally Important Crops," Cold Spring Harbor Laboratory, p. 120 (1988); Hilder, et al., "A Novel Mechanism of Insect Resistance Engineered into Tobacco," *Nature*, 330:160–63 (1987); Ryan, C. A., "Proteinase Inhibitor Gene Families: Strategies for Transformation to Improve Plant Defenses Against Herbivores," *BioEssays*, 10:20–24 (1989); Vaeck, et al., "Transgenic Plants Protected from Insect Attack," *Nature*, 328:33–27 (1987).

One target that has been selected is a structural polymer, chitin, which is present in insects and some fungi that attack plants, but is absent in higher plants and vertebrates. U.S. Pat. No. 4,751,081 follows this approach and is directed to novel chitinase producing bacteria strains for use in inhibiting chitinase sensitive plant pathogens (i.e. fungi and nematodes). However, the approach of U.S. Pat. No. 4,751,081 lacks flexibility.

The present invention is directed to controlling fungi and insects that attack plants.

SUMMARY OF THE INVENTION

The present invention relates to isolated DNA molecules encoding chitinolytic enzymes, which have chitinolytic activity under alkaline conditions, as well as to vectors, host cells, and transgenic plants and plant seeds transformed with these DNA molecules.

Another aspect of the present invention relates to a method of insect and/or fungus control for plants. This method involves applying the chitinolytic enzymes to plants or plant seeds under conditions effective to control insects and/or fungi on the plants or plants grown from the plant seeds.

As an alternative to applying the chitinolytic enzymes to plants or plant seeds in order to control insects and/or fungi on plants or plants grown from the seeds, transgenic plants or plant seeds can be utilized. When utilizing transgenic plants, this involves providing a transgenic plant transformed with a DNA molecule encoding a chitinolytic enzyme and growing the plant under conditions effective to control insects and/or fungi. Alternatively, a transgenic plant seed transformed with a DNA molecule encoding the chitinolytic enzyme can be provided and planted in soil. A plant is then propagated from the planted seed under conditions effective to control insects and/or fungi.

The present invention is directed to effecting any form of insect and/or fungus control for plants.

For example, insect control or fungus control according to the present invention encompasses preventing insects or fungi from contacting plants to which the chitinolytic enzymes have been applied, preventing direct damage to plants by feeding injury, causing insects or fungi to depart from such plants, killing insects or fungi proximate to such plants, interfering with feeding on plants by insects or fungi, preventing insects or fungi from colonizing host plants, preventing colonizing insects or fungi from releasing phytotoxins, etc. The present invention also prevents subsequent disease damage to plants resulting from insect or fungal invasion.

As a result, the present invention provides significant economic benefit to growers.

BRIEF DESCRIPTION OF THE DRAWINGS

FIG. 1A indicates endochitinase activity (units/ml), FIG. 1B indicates chitobiosidase activity (% nkatals), and FIG. 1C indicates glucosaminidase activity (% nkatals) at pH 9. These are representative data; the experiment was replicated twice with similar results.

FIG. 2A shows native gel with Coomassie stain, while FIG. 2B shows native gel with overlay of fluorogenic substrate for endochitinases and chitobiosidases. C indicates the chitobiosidase band, G indicates the glucosaminidase band, and E indicates the endochitinase bands. These are representative data; the experiment was replicated 2 times with similar results.

FIG. 10A shows Coomassie stain to detect all proteins. FIG. 10B shows fluorogenic overlay to locate enzymes with chitinolytic activity. Based on previous experiments (Broadway, et al., "Partial Characterization of Chitinolytic Enzymes from *Streptomyces albidoflavus*," *Lett. Appl. Microbiol.*, 20:271–76 (1995), which is hereby incorporated by reference), the upper (most acidic) two bands were chitobiosidases, while the lower (most alkaline) five bands were endochitinases.

DETAILED DESCRIPTION OF THE INVENTION

Figure 1A:
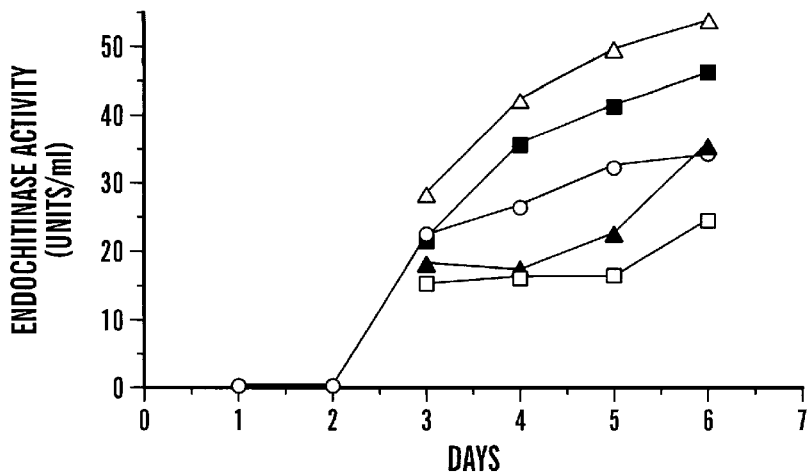
FIGS. 1A to C show a time course of chitinolytic enzyme activity in culture filtrate from *Streptomyces albidoflavus* NRRL B-16746 and NRRL 21918. The liquid medium contained 0.5% chitin, while the glucose component was 0% (solid square), 0.01% (open triangle), 0.1% (open circle), 0.25% (solid triangle), and 0.5% (open square).

Chitin, an insoluble linear β-1,4-linked polymer of N-acetyl-β-D-glucosamine, is a structural polysaccharide that is present in all arthropods, yeast, most fungi, and some stages of nematodes. Chitinolytic enzymes are proteins that catalyze the hydrolysis of chitin by cleaving the bond between the C1 and C4 of two consecutive N-acetylglucosamines. There are three types of chitinolytic enzyme activity: (1) N-acetyl-β-glucosaminidase (i.e., EC 3.2.1.30, abbreviated glucosaminidase), which cleaves monomeric units from the terminal end of chitin, (2) 1,4-β-chitobiosidase (i.e., abbreviated chitobiosidase), which cleaves dimeric units from the terminal end of chitin, and (3) endochitinase (EC 3.2.1.14), which randomly cleaves the chitin molecule internally (Sahai, et al., "Chitinases of Fungi and Plants: Their Involvement in Morphogenesis and Host-Parasite Interaction," *FEMS Microbiol. Rev.*, 11:317–38 (1993), which is hereby incorporated by reference). Two or three types of enzymes are often synthesized by a single organism (Harman, et al., "Chitinolytic Enzymes of *Trichoderma harzianum*: Purification of Chitobiase and Endochitinase," *Phytopathology*, 83:313–18 (1993), Neugebauer, et al., "Chitinolytic Properties of *Streptomyces lividans*," *Arch. Microbiol*, 156:192–97 (1991), Romaguera, et al., "Protoplast Formation by a Mycolase from *Streptomyces olivaceoviridis* and Purification of Chitinases," *Enzyme Microb. Technol.*, 15:412–17 (1993), which are hereby incorporated by reference), which may enhance the speed and/or efficiency of degradation of chitin.

The chitinolytic enzymes of the present invention are particularly effective in controlling insects, because they are active under alkaline conditions. As a result, these enzymes can be ingested by insects and then attack the insects by degrading their chitin-containing, alkaline digestive tracts.

The present invention relates to chitinolytic enzymes which are active under alkaline conditions (i.e. at a pH greater than 7) alone but may also be active under neutral and/or acid conditions. The present invention also encompasses the DNA molecules encoding these enzymes. Examples of such chitinolytic enzymes are the following enzymes isolated from *Streptomyces albidoflavus* which have either chitobiosidase or endochitinase activity.

The chitobiosidase isolated from *Streptomyces albidoflavus* has an amino acid sequence of SEQ. ID. No. 1 as follows:

```
Ala Pro Ala Ala Val Pro Ala His Ala Val Thr Gly Tyr Trp Gln Asn
1               5                   10                  15

Phe Asn Asn Gly Ala Thr Val Gln Thr Leu Ala Asp Val Pro Asp Ala
            20                  25                  30

Tyr Asp Ile Ile Ala Val Ser Phe Ala Asp Ala Thr Ala Asn Ala Gly
            35                  40                  45

Glu Ile Thr Phe Thr Leu Asp Ser Val Gly Leu Gly Gly Tyr Thr Asp
    50                      55                  60

Glu Gln Phe Arg Ala Asp Leu Ala Ala Lys Gln Ala Asp Gly Lys Ser
65                      70                  75                  80

Val Ile Ile Ser Val Gly Gly Glu Lys Gly Ala Val Ala Val Asn Asp
                85                  90                  95

Ser Ala Ser Ala Gln Arg Phe Ala Asp Ser Thr Tyr Ala Leu Met Glu
                100                 105                 110

Glu Tyr Gly Phe Asp Gly Val Asp Ile Asp Leu Glu Asn Gly Leu Asn
            115                 120                 125

Ser Thr Tyr Met Thr Glu Ala Leu Thr Lys Leu His Glu Lys Ala Gly
    130                     135                 140

Asp Gly Leu Val Leu Thr Met Ala Pro Gln Thr Ile Asp Met Gln Ser
145                     150                 155                 160

Pro Glu Asn Glu Tyr Phe Lys Thr Ala Leu Val Thr Lys Asp Phe Leu
            165                 170                 175

Thr Ala Val Asn Met Gln Tyr Tyr Asn Ser Gly Ser Met Leu Gly Cys
            180                 185                 190

Asp Gly Gln Val Tyr Ala Gln Gly Thr Val Asp Phe Leu Thr Ala Leu
            195                 200                 205

Ala Cys Ile Gln Leu Glu Asn Gly Leu Asp Ala Ser Gln Val Gly Ile
        210                 215                 220

Gly Val Pro Ala Ser Pro Lys Ala Ala Gly Gly Gly Tyr Val Glu Pro
225                 230                 235                 240

Ser Val Val Asn Asp Ala Leu Asp Cys Leu Thr Arg Gly Thr Gly Cys
                245                 250                 255

Gly Ser Phe Lys Pro Glu Lys Thr Tyr Pro Ala Leu Arg Gly Ala Met
            260                 265                 270
```

-continued
Thr Trp Ser Thr Asn Trp Asp Ala Asp Thr Gly Asn Ala Trp Ser Asn
        275                 280                 285

Val Val Gly Pro His Val Asp Asp Leu Pro
        290                 295

The chitobiosidase has a molecular mass of 34 kD and an isoelectric point of less than 3.0.

The chitobiosidase isolated from *Streptomyces albidoflavus* having an amino acid sequence of SEQ. ID. No. 1 is encoded by a DNA molecule having a nucleotide sequence of SEQ. ID. No. 2 as follows:

```
GCGGCCGCTC CGGGCGGACG ACCGTACGGA CTCCTCGGCC GACCCCTGCG GGAACCCTTG    60
ACAACCCCAT TGGTCTGGAC CAGTTTGGTG CCCATCGCGG TGGCCACCGT GCGCCAACTC   120
CCCGCCCCCT CCCGGGTGGC GGGCCCCGTC GGCGCGTCCC CCCACGTCCG TGACTCCCCC   180
CACCGGAGGC AGCAGTGGTA CGCACCTACC CCCTTCCGCA CCCCGGCCGG CGCCCCTCCA   240
CGCCCGGCCT CCACCGCAGG GGCCGGCTGA CCGCCGCCCT CACCGCGGCC GTCCTCGGCG   300
CCTCCGGGCT CGCCCTCACC GGCCCCGCGA CCGCCGGCGA GGGGGCCCCC GCCGCCCAGG   360
CCGCCCCGGC CGCCGTACCG GCCCACGCGG TGACCGGTTA CTGGCAGAAC TTCAACAACG   420
GCGCGACCGT GCAGACCCTC GCCGACGTGC CGGACGCCTA CGACATCATC GCCGTCTCCT   480
TCGCCGACGC CACGGCCAAC GCGGGCGAGA TCACCTTCAC CCTCGACTCG GTCGGGCTCG   540
GCGGCTACAC CGACGAGCAG TTCCGCGCCG ACCTCGCCGC CAAGCAGGCC GACGGCAAGT   600
CGGTGATCAT CTCGGTCGGC GGCGAGAAGG GCGCGGTCGC CGTCAACGAC AGCGCCTCCG   660
CCCAGCGCTT CGCCGACAGC ACCTACGCGC TGATGGAGGA GTACGGCTTC GACGGCGTCG   720
ACATCGACCT GGAGAACGGC CTCAACTCCA CCTACATGAC CGAGGCCCTC ACCAAGCTCC   780
ACGAGAAGGC CGGGGACGGC CTGGTCCTCA CCATGGCGCC GCAGACCATC GACATGCAGT   840
CGCCCGAGAA CGAGTACTTC AAGACGGCGC TGGTCACGAA AGACTTCCTG ACCGCCGTCA   900
ACATGCAGTA CTACAACAGC GGCTCGATGC TCGGCTGCGA CGGCCAGGTC TACGCGCAGG   960
GCACCGTCGA CTTCCTCACC GCGCTCGCCT GCATCCAGCT GGAGAACGGT CTCGACGCCT  1020
CCCAGGTCGG CATCGGTGTC CCCGCCTCCC CGAAGGCGGC CGGCGGCGGC TACGTCGAGC  1080
CCTCCGTGGT CAACGACGCG CTGGACTGCC TGACCCGGGG CACCGGTTGT GGCTCGTTCA  1140
AGCCGGAGAA GACCTACCCG GCGCTGCGTG GCGCCATGAC CTGGTCGACC AACTGGGACG  1200
CCGACACCGG CAACGCCTGG TCGAACGTGG TCGGCCCGCA CGTCGACGAC CTGCCGTAAC  1260
CCCGGAGCCG GGCACCCGTC CGCTTCCCCC GCAC                              1294
```

The endochitinase isolated from *Streptomyces albidoflavus* has an amino acid sequence of SEQ. ID. No. 3 as follows:

```
Gly Pro Gly Pro Gly Pro Arg Glu Lys Ile Asn Leu Gly Tyr Phe Thr
1               5                   10                  15

Glu Trp Gly Val Tyr Gly Arg Asn Tyr His Val Lys Asn Leu Val Thr
            20                  25                  30

Ser Gly Ser Ala Glu Lys Ile Thr His Ile Asn Tyr Ser Phe Gly Asn
            35                  40                  45

Val Gln Gly Gly Lys Cys Thr Ile Gly Asp Ser Phe Ala Ala Tyr Asp
            50                  55                  60

Lys Ala Tyr Thr Ala Ala Glu Ser Val Asp Gly Val Ala Asp Thr Trp
65                  70                  75                  80

Asp Gln Pro Leu Arg Gly Asn Phe Asn Gln Leu Arg Lys Leu Lys Ala
                85                  90                  95

Lys Tyr Pro His Ile Lys Val Leu Trp Ser Phe Gly Trp Thr Trp
                100                 105                 110

Ser Gly Gly Phe Thr Asp Ala Val Lys Asn Pro Ala Ala Phe Ala Lys
            115                 120                 125

Ser Cys His Asp Leu Val Glu Asp Pro Arg Trp Ala Asp Val Phe Asp
            130                 135                 140

Gly Ile Asp Leu Asp Trp Glu Tyr Pro Asn Ala Cys Gly Leu Ser Cys
145                 150                 155                 160

Asp Ser Ser Gly Pro Ala Ala Leu Lys Asn Met Val Gln Ala Met Arg
                165                 170                 175

Ala Gln Phe Gly Thr Asp Leu Val Thr Ala Ala Ile Thr Ala Asp Ala
            180                 185                 190

Ser Ser Gly Gly Lys Leu Asp Ala Ala Asp Tyr Ala Gly Ala Ala Gln
            195                 200                 205

Tyr Phe Asp Trp Tyr Asn Val Met Thr Tyr Asp Phe Phe Gly Ala Trp
            210                 215                 220

Asp Lys Thr Gly Pro Thr Ala Pro His Ser Ala Leu Asn Ser Tyr Ser
225                 230                 235                 240

Gly Ile Pro Lys Ala Asp Phe His Ser Ala Ala Ile Ala Lys Leu
                245                 250                 255

Lys Ala Lys Gly Val Pro Ala Ser Lys Leu Leu Leu Gly Ile Gly Phe
            260                 265                 270

Tyr Gly Arg Gly Trp Thr Gly Val Thr Gln Asp Ala Pro Gly Gly Thr
            275                 280                 285

Ala Thr Gly Pro Ala Thr Gly Thr Tyr Glu Ala Gly Ile Glu Asp Tyr
            290                 295                 300

Lys Val Leu Lys Asn Thr Cys Pro Ala Thr Gly Thr Val Gly Gly Thr
305                 310                 315                 320

Ala Tyr Ala Lys Cys Gly Ser Asn Trp Trp Ser Tyr Asp Thr Pro Ala
                325                 330                 335

Thr Ile Lys Thr Lys Met Thr Trp Ala Lys Asp Gln Gly Leu Gly Gly
                340                 345                 350

Ala Phe Phe Trp Glu Phe Ser Gly Asp Thr Ala Gly Gly Glu Leu Val
            355                 360                 365

Ser Ala Met Asp Ser Gly Leu Arg
            370                 375
```

The endochitinase has a molecular mass of 45 kD and an isoelectric point of about 6.5.

The endochitinase isolated from *Streptomyces albidoflavus* having an amino acid sequence of SEQ. ID. No. 3 is encoded by a DNA molecule having a nucleotide sequence of SEQ. ID. No. 4 as follows:

```
GTCGACTGGT ACAACGTGAT GACCTACGAC TACTTCGGCA CCTGGGCCGC CCAGGGCCCG   60
ACGGCGCCCC ACTCGCCGCT CACCGCCTAC CCGGGCATCC AGGGCGAGCA CAACACCTCC  120
TCGGCCACCA TCGCCAAGCT GCGGGGCAAG GGCATCCCGG CGAAGAAGCT GCTGCTGGGC  180
ATCGGCGCCT ACGGCCGCGG CTGGACCGGC GTCACCCAGG ACGCCCCGG CGGCACCGCC  240
ACCGGCCCGG CCGCCGGCAC CTACGAGGCG GGCAACGAGG AGTACCGGGT GCTGGCCGAG  300
AAGTGCCCGG CCACCGGCAC CGCCGGCGGC ACCGCGTACG CCAAGTGCGG CGACGACTGG  360
TGGAGTTACG ACACCCCTGA GACGGTGACG GGCAAGATGG CCTGGGCGAA GAAGCAGAAG  420
CTCGGCGGTG CCTTCCTCTG GGAGTTCGCC GGCGACGGCG CCAAGGGCGA TCTGTTCAGG  480
GCGATGCACG AGGGGCTGCG CTGACCGGCC GGGCACTCAC CCGGAACTGA CCCTTCCCGC  540
ACGGCCGTCC GCCGTGGCAC CGGAGCTCCG GTCGCCGCGG CGGGCGGCCG TGTCCGCATG  600
TCGCCACCCC CGCGCACCAG GCGCGATCCG GCCGAACTTT CCTTTGGTCC AGACCTCTTG  660
ACCTCTGGTC CAGACCTTTT CTACTCTCGC CCCACTGCGG TGGGCACATC GGTCGTCGGT  720
GCTCACGGGC GTCGCAGGGT TCCGCCCCCA TACGTCCGGA CCTCTTGAGG AGTACGCCTT  780
GAGTACGGTT TCCCCCAGCA CCGACGGCGC CCGCAGCCGT CCCAGACCCC TCAGCCGCTT  840
CCGCCGGCGC GCGCTGGCCG CGCTCGTCGG CCTCGCGGTC CCCTTCGCCG GGATGGTCGG  900
CCTCGCCGCC CCCACCCAGG CCGCCGAGGC CGCGGCCGAC CCCAGCGCCT CCTACACCAG  960
GACGCAGGAC TGGGGCAGCG GCTTCGAGGG CAAGTGGACG GTGAAGAACA CCGGCACCGC 1020
CCCCCTCAGC GGCTGGACCC TGGAGTGGGA CTTCCCCGCC GGAACCAAGG TGACCTCGGC 1080
CTGGGACGCC GACGTCACCA ACAACGGCGA CCACTGGACC GCCAAGAACA AGAGCTGGGC 1140
GGGGAGCCTC GCCCCCGGCG CCTCGGTCAG CTTCGGCTTC AACGGCACCG GCCCCGGCAC 1200
CCCCTCGGGC TGCAAGCTCA ACGGCGCCTC CTGCGACGGC GGCAGCGTCC CCGGCGACAC 1260
CCCGCCCACC GCCCCCGGCA CCCCCACCGC CAGTGACCTC ACCAAGAACT CGGTGAAGCT 1320
CTCCTGGAAG GCGGCCACCG ACGACAAGGG CGTCAAGAAC TACGACGTCC TGCGCGACGG 1380
CGCCAAGGTC GCCACCGTCA CCGCCACCAC CTTCACCGAC CAGAACCTCG CCCCCGGCAC 1440
CGACTACTCC TACTCGGTCC AGGCCCGCGA CACCGCCGAC CAGACCGGCC CGGTCAGCGC 1500
CCCCGTCAAG GTCACCACCC CCGGCGACGG CACGGGCCCC GGCCCCGGCC CCGCGAGAA 1560
GATCAACCTC GGCTACTTCA CCGAGTGGGG CGTCTACGGC CGCAACTACC ACGTCAAAAA 1620
CCTGGTGACC TCCGGCTCCG CCGAGAAGAT CACCCACATC AACTACTCCT TCGGCAACGT 1680
CCAGGGCGGC AAGTGCACCA TCGGTGACAG CTTCGCCGCC TACGACAAGG CGTACACCGC 1740
CGCCGAGTCG GTCGACGGCG TCGCCGACAC CTGGGACCAG CCGCTGCGCG GCAACTTCAA 1800
CCAGCTCCGC AAGCTCAAGG CCAAGTACCC GCACATCAAG GTCCTCTGGT CCTTCGGCGG 1860
CTGGACCTGG TCCGGCGGCT TCACCGACGC CGTGAAGAAC CCGGCCGCCT TCGCCAAGTC 1920
CTGCCACGAC CTGGTCGAGG ACCCGCGCTG GGCCGACGTC TTCGACGGCA TCGACCTCGA 1980
CTGGGAGTAC CCGAACGCCT GCGGCCTCAG CTGCGACAGC TCCGGTCCGG CCGCGCTGAA 2040
GAACATGGTC CAGGCGATGC GCGCCCAGTT CGGCACCGAC CTGGTCACCG CCGCCATCAC 2100
CGCCGACGCC AGCTCCGGCG GCAAGCTCGA CGCCGCCGAC TACGCGGGCG CCGCCCAGTA 2160
```

-continued

```
CTTCGACTGG TACAACGTGA TGACGTACGA CTTCTTCGGC GCCTGGGACA AGACCGGCCC 2220

GACCGCGCCC CACTCGGCCC TGAACTCCTA CAGCGGCATC CCCAAGGCCG ACTTCCACTC 2280

GGCCGCCGCC ATCGCCAAGC TCAAGGCGAA GGGCGTCCCG GCGAGCAAGC TCCTGCTCGG 2340

CATCGGCTTC TACGGCCGCG GCTGGACCGG CGTCACCCAG GACGCCCCGG GCGGCACCGC 2400

CACCGGCCCG GCCACCGGCA CCTACGAGGC GGGCATCGAG GACTACAAGG TCCTCAAGAA 2460

CACCTGCCCC GCCACCGGCA CCGTCGGCGG CACCGCGTAC GCCAAGTGCG GCAGCAACTG 2520

GTGGAGCTAC GACACCCCGG CCACCATCAA GACCAAGATG ACCTGGGCCA AGGACCAGGG 2580

CCTCGGCGGC GCCTTCTTCT GGGAGTTCAG CGGTGACACC GCGGGCGGCG AACTGGTCTC 2640

CGCGATGGAC TCCGGCCTCC GCTAGCCCCG GACCGGCACC CCGCCCGAAC CACTAGCACG 2700

ACCTCCCCCG GA                                                   2712
```

Fragments of the above chitinolytic enzymes are encompassed by the present invention.

Suitable fragments can be produced by several means. In the first, subclones of the gene encoding the chitinolytic enzymes of the present invention are produced by conventional molecular genetic manipulation by subcloning gene fragments. The subclones then are expressed in vitro or in vivo in bacterial cells to yield a smaller protein or peptide that can be tested for chitinolytic activity according to the procedure described below.

As an alternative, fragments of a chitinolytic enzyme can be produced by digestion of a full-length chitinolytic enzyme with proteolytic enzymes like chymotrypsin or Staphylococcus proteinase A, or trypsin. Different proteolytic enzymes are likely to cleave chitinolytic enzymes at different sites based on the amino acid sequence of the chitinolytic enzyme. Some of the fragments that result from proteolysis may be active chitinolytic enzymes.

In another approach, based on knowledge of the primary structure of the protein, fragments of a chitinolytic enzyme encoding gene may be synthesized by using the PCR technique together with specific sets of primers chosen to represent particular portions of the protein. These then would be cloned into an appropriate vector for increased expression of a truncated peptide or protein.

Chemical synthesis can also be used to make suitable fragments. Such a synthesis is carried out using known amino acid sequences for a chitinolytic enzyme being produced. Alternatively, subjecting a full length chitinolytic enzyme to high temperatures and pressures will produce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure and hydropathic nature of an enzyme. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Suitable DNA molecules are those that hybridize to a DNA molecule comprising a nucleotide sequence of SEQ. ID. Nos. 2 or 4 under stringent conditions. An example of suitable stringency conditions is when hybridization is carried out at 65° C. for 20 hours in a medium containing 1M NaCl, 50 mM Tris-HCl, pH 7.4, 10 mM EDTA, 0.1% sodium dodecyl sulfate, 0.2% ficoll, 0.2% polyvinylpyrrolidone, 0.2% bovine serum albumin, 50 μm g/ml E. coli DNA.

A chitinolytic enzyme of the present invention is preferably produced in purified form (preferably at least about 80%, more preferably 90%, pure) by conventional techniques. Typically, a chitinolytic enzyme of the present invention is secreted into the growth medium of recombinant host cells. Alternatively, a chitinolytic enzyme of the present invention is produced but not secreted into growth medium. In such cases, to isolate a chitinolytic enzyme, the host cell (e.g., E. coli) carrying a recombinant plasmid is propagated, lysed by sonication, heat, differential pressure, or chemical treatment, and the homogenate is centrifuged to remove bacterial debris. The supernatant is then subjected to sequential ammonium sulfate precipitation. The fraction containing a chitinolytic enzyme of the present invention is subjected to gel filtration in an appropriately sized dextran or polyacrylamide column to separate the proteins. If necessary, the protein fraction may be further purified by HPLC.

The DNA molecule encoding a chitinolytic enzyme can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK± or KS± (see "Stratagene Cloning Systems"

Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual,* Cold Springs Laboratory, Cold Springs Harbor, New York (1989), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology,* 68:473 (1979), which is hereby incorporated by reference.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli,* its bacteriophages, or plasmids, promoters such as the T7 phage promoter, lac promotor, trp promotor, recA promotor, ribosomal RNA promotor, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires an SD sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once an isolated DNA molecule encoding a chitinolytic enzyme has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The present invention further relates to a method of effecting insect and/or fungus control for plants. This method involves applying a chitinolytic enzyme to all or part of a plant or a plant seed under conditions effective to control insects and/or fungi. Alternatively, the chitinolytic enzyme can be applied to plants such that seeds recovered from such plants themselves are able to effect insect and/or fungus control.

As an alternative to applying a chitinolytic enzyme to plants or plant seeds in order to control insects and/or fungi on the plants or plants grown from the seeds, transgenic plants or plant seeds can be utilized. When utilizing transgenic plants, this involves providing a transgenic plant transformed with a DNA molecule encoding a chitinolytic enzyme and growing the plant under conditions effective to permit that DNA molecule to control insects and/or fungi. Alternatively, a transgenic plant seed transformed with a DNA molecule encoding a chitinolytic enzyme can be provided and planted in soil. A plant is then propagated from the planted seed under conditions effective to control insects and/or fungi.

The embodiment of the present invention where the chitinolytic enzyme is applied to the plant or plant seed can be carried out in a number of ways, including: 1) application of an isolated chitinolytic enzyme and 2) application of bacteria which do not cause disease and are transformed with genes encoding a chitinolytic enzyme.

In one embodiment of the present invention, a chitinolytic enzyme of the present invention can be isolated (i.e. separated from the bacteria which naturally produce it) as described in the Examples infra. Preferably, however, an isolated chitinolytic enzyme of the present invention is produced recombinantly and purified (i.e. made substantially free of contaminants) as described supra.

In another embodiment of the present invention, a chitinolytic enzyme of the present invention can be applied to plants or plant seeds by applying bacteria containing genes encoding a chitinolytic enzyme. Such bacteria must be capable of secreting or exporting the enzyme so that the enzyme can effect fungus and/or insect control. In these embodiments, the chitinolytic enzyme is produced by the bacteria in planta or on seeds or just prior to introduction of the bacteria to the plants or plant seeds.

In the bacterial application mode of the present invention, the bacteria do not cause the disease and have been transformed (e.g., recombinantly) with a gene encoding a chitinolytic enzyme. For example, *E. coli* can be transformed with a gene encoding a chitinolytic enzyme and then applied to plants. Bacterial species other than *E. coli* can also be used in this embodiment of the present invention.

The method of the present invention can be utilized to treat a wide variety of plants or their seeds to control fungi and/or insects. Suitable plants include dicots and monocots. Monocots treatable in accordance with the present invention include Gramineae (e.g., grass, corn, grains, bamboo, sugar cane), Liliaceae (e.g., onion, garlic, asparagus, tulips, hyacinths, day lily, and aloes), Iridaceae (e.g., iris, gladioli, freesia, crocus, and watsonia), and Orchidacea (e.g., orchid). Examples of dicots which can be treated pursuant to the present invention include Salicaceae (e.g., willow, and poplar), Ranunculaceae (e.g., Delphinium, Paeonia, Ranunculus, Anemone, Clematis, columbine, and marsh marigold), Magnoliaceae (e.g., tulip tree and Magnolia), Cruciferae (e.g., mustards, cabbage, cauliflower, broccoli, brussel sprouts, kale, kohlrabi, turnip, and radish), Rosaceae (e.g., strawberry, blackberry, peach, apple, pear, quince, cherry, almond, plum, apricot, and rose), Leguminosae (e.g., pea, bean, peanut, alfalfa, clover, vetch, redbud, broom, wisteria, lupine, black locust, and acacia), Malvaceae (e.g., cotton, okra, and mallow), Umbelliferae (e.g., carrot, parsley, parsnips, and hemlock), Labiatae (e.g., mint, peppermints, spearmint, thyme, sage, and lavender), Solanaceae (e.g., potato, tomato, pepper, eggplant, and Petunia), Cucurbitaceae (e.g., melon, squash, pumpkin, and cucumber), Compositae (e.g., sunflower, endive, artichoke, lettuce, safflower, aster, marigold, dandelions, sage brush, Dalia, Chrysanthemum, and Zinna), and Rubiaceae (e.g., coffee).

The present invention is effective against a wide variety of insect pests including the orders of Lepidoptera, Coleoptera, Diptera, Homoptera, Hemiptera, Thysanoptera, and Orthoptera. Examples of Lepidoptera include butterflies and moths. Coleoptera include beetles. Examples of Diptera are flies. Examples of Homoptera are aphids, whiteflies, scales, psyllids, leafhoppers, plant hoppers, cicadas, and treehoppers. The Hemiptera which are treatable in accordance with the present invention include true bugs. Thysanoptera which can be treated in accordance with the present invention include thrips. Examples of Orthoptera which can be treated in accordance with the present invention are grasshoppers, crickets, and katydids. Collectively, these orders of insect pests represent the most economically important group of pests for vegetable production worldwide.

The chitin-containing fungi inhibited by the purified chitinases of the present invention include, for example, species from the genera including Fusarium, Gliocadium, Rhizoctonia, Trichoderma, Uncinula, Ustilago, Erysiphe, Botrytis, Saccharomyces, Sclerotium, and Alternaria.

The method of the present invention involving application of a chitinolytic enzyme can be carried out through a variety of procedures when all or part of the plant is treated, including leaves, stems, roots, etc. This may (but need not) involve infiltration of the chitinolytic enzyme into the plant. Suitable application methods include topical application (e.g., high or low pressure spraying), injection, and leaf abrasion proximate to when enzyme application takes place. When treating plant seeds, in accordance with the application embodiment of the present invention, a chitinolytic enzyme can be applied by low or high pressure spraying, coating, immersion, or injection. Other suitable application procedures can be envisioned by those skilled in the art provided they are able to effect contact of the chitinolytic enzyme with the plant or plant seed. Once treated with a chitinolytic enzyme of the present invention, the seeds can be planted in natural or artificial soil and cultivated using conventional procedures to produce plants. After plants have been propagated from seeds treated in accordance with the present invention, the plants may be treated with one or more applications of a chitinolytic enzyme to control insects and/or fungi on the plants.

The chitobiosidase or endochitinase can be applied to plants or plant seeds in accordance with the present invention individually, in combination with one another, or in a mixture with other materials. Alternatively, a chitinolytic enzyme can be applied separately to plants with other materials being applied at different times.

A composition suitable for treating plants or plant seeds in accordance with the application embodiment of the present invention contains a chitinolytic enzyme in a carrier. Suitable carriers include water, aqueous solutions, slurries, or dry powders. In this embodiment, the composition contains greater than 500 nM chitinolytic enzyme.

Although not required, this composition may contain additional additives including fertilizer, insecticide, fungicide, nematacide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and abrading agents. These materials can be used to facilitate the process of the present invention. In addition, a chitinolytic enzyme can be applied to plant seeds with other conventional seed formulation and treatment materials, including clays and polysaccharides.

In the alternative embodiment of the present invention involving the use of transgenic plants and transgenic seeds, a chitinolytic enzyme need not be applied topically to the plants or seeds. Instead, transgenic plants transformed with a DNA molecule encoding a chitinolytic enzyme are produced according to procedures well known in the art.

In producing transgenic plants, the DNA construct in a vector described above can be microinjected directly into plant cells by use of micropipettes to transfer mechanically the recombinant DNA. Crossway, *Mol. Gen. Genetics,* 202:179–85 (1985), which is hereby incorporated by reference. The genetic material may also be transferred into the plant cell using polyethylene glycol. Krens, et al., *Nature,* 296:72–74 (1982), which is hereby incorporated by reference.

Another approach to transforming plant cells with the DNA construct is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, a vector containing the DNA construct can be introduced into the cell by coating the particles with the vector containing that heterologous DNA construct. Alternatively, the target cell can be surrounded by the vector so that the vector is carried into the cell by the wake of the particle. Biologically active particles (e.g., dried bacterial cells containing the vector and heterologous DNA construct) can also be propelled into plant cells.

Yet another method of introduction is fusion of protoplasts with other entities, either minicells, cells, lysosomes or other fusible lipid-surfaced bodies. Fraley, et al., *Proc. Natl. Acad. Sci. USA,* 79:1859–63 (1982), which is hereby incorporated by reference.

The DNA molecule may also be introduced into the plant cells by electroporation. Fromm et al., *Proc. Natl. Acad. Sci. USA,* 82:5824 (1985), which is hereby incorporated by reference. In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

Agrobacterium is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes.* The Ti or Ri plasmid is transmitted to plant cells on infection by Agrobacterium and is stably integrated into the plant genome. J. Schell, *Science,* 237:1176–83 (1987), which is hereby incorporated by reference.

After transformation, the transformed plant cells must be regenerated.

Plant regeneration from cultured protoplasts is described in Evans et al., *Handbook of Plant Cell Cultures, Vol.* 1: (MacMillan Publishing Co., New York, 1983); and Vasil I. R. (ed.), *Cell Culture and Somatic Cell Genetics of Plants,* Acad. Press, Orlando, Vol. I, 1984, and Vol. III (1986), which are hereby incorporated by reference.

It is known that practically all plants can be regenerated from cultured cells or tissues, including but not limited to, all major species of sugarcane, sugar beets, cotton, fruit trees, and legumes.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure so that the DNA construct is present in the resulting plants. Alternatively, transgenic seeds are recovered from the transgenic plants. These seeds can then be planted in the soil and cultivated using conventional procedures to produce transgenic plants.

When transgenic plants and plant seeds are used in accordance with the present invention, they additionally can be treated with the same materials as are used to treat the plants and seeds to which a chitinolytic enzyme is applied. These other materials, including a chitinolytic enzyme, can be applied to the transgenic plants and plant seeds by the above-noted procedures, including high or low pressure spraying, injection, coating, and immersion. Similarly, after plants have been propagated from the transgenic plant seeds, the plants may be treated with one or more applications of a chitinolytic enzyme to control fungi and/or insects. Such plants may also be treated with conventional plant treatment agents (e.g., insecticides, fertilizers, etc.). The transgenic plants of the present invention are useful in producing seeds or propagules (e.g., cuttings) from which fungus and/or insect resistant plants grow.

EXAMPLES

Example 1

Bacteria

Bacterial strains were grown on slants of trypticase soy agar (BBL, Cockeysville, Md.) for maintenance of cultures and production of inoculum. Growth from agar slants was transferred to a liquid medium consisting of 50 mM magnesium sulfate, 0.1% glucose, 0.1% calcium chloride, 0.05% manganese sulfate, 0.025% ferrous sulfate, 0.00125% zinc sulfate, and 0.5% crab shell chitin. The cultures were grown in flasks with constant shaking at 30 C for 4–5 days, or in an 18 liter fermenter (Microfilm Model MF 214, New Brunswick Scientific Co., New Brunswick N.J.) at 30–30 C, air flow of 200–400 cc min$^{-1}$, and impeller speed of 150 rpm for 5 days.

Example 2

Survey of Chitinolytic Enzymes with Activity in an Alkaline Environment

Over 100 strains of microorganisms from alkaline soil were screened for their ability to clear chitin-containing agar plates buffered at pH 9. From this survey, a strain of Streptomyces was isolated that secreted chitinolytic enzymes which were active at pH 9, when the strain was grown on chitin-containing agar plates (pH 9) or liquid culture medium (pH 9) containing chitin.

Example 3

Characterization of Active Strain

The active Streptomyces species was evaluated by the standard taxonomic criteria of the International Streptomyces Project (Shirling, et al., "Methods for Characterization of Streptomyces Species," *Int. J. Syst. Bacteriol.*, 16:313–40 (1966), which is hereby incorporated by reference), including (a) growth on yeast extract-malt extract agar, inorganic salts-starch agar, glycerol-asparagine agar and Czapek's agar, (b) production of melanin pigments, and (c) utilization of 11 different carbohydrates as the sole carbon source. The strain was also grown for 4 days at 28 C on trypticase soy broth agar plates, the biomass scraped from the plates. Saponification of the cells and methylation of the fatty acids were done according to the method of Korn-Wendisch et al. (Korn-Wendisch, et al., "Transfer of *Faenia rectivirgula* Kurup and Agre 1983 to the Genus Saccharopolyspora Lacey and Goodfellow 1975, Elevation of *Saccharopolyspora hirsuta* subsp. *taberi* Labeda 1987 to Species Level, and Emended Description of the Genus *Saccharopolyspora*," *Int. J. Syst. Bacteriol.*, 39:430–41 (1989), which is hereby incorporated by reference), and the profile of fatty acid methyl esters present in the extracts was determined by gas chromatography using an HP 5890A gas chromatograph fitted with 25 m×0.2 mm phenyl methyl silicone fused silica capillary column (Hewlett-Packard, Inc., Palo Alto, Calif.) and Microbial Identification System software (Microbial ID, Inc., Newark, Del.), using the standard calibration mixture provided by the manufacturer. The fatty acid methyl ester profile observed for this strain was compared with those in the ACTINO library provided with the Microbial Identification System, as well as with in-house STMYB9 Streptomyces profile library.

The active strain was identified as a member of *Streptomyces albidoflavus*, based of morphological and physiological characteristics, and fatty acid profile (Table 1).

TABLE 1

Comparison of fatty acid profiles between Streptomyces strain NRRL B-16746 and that of the library entry for *Streptomyces albidoflavus*.

| Fatty Acid | S. albidoflavus Library Entry | Streptomyces sp. NRRL B-16746 |
|---|---|---|
| 14:0 iso | 5.92–25.81 | 6.47 |
| 15:0 iso | 2.50–9.50 | 7.38 |
| 15:0 anteiso | 6.74–29.26 | 26.35 |
| 15:1 B | 0.00–5.55 | 2.55 |
| 15:0 | 2.55–10.80 | 3.84 |
| 16:1 iso H | 3.30–18.70 | 4.99 |
| 16:1 iso | 14.84–33.30 | 18.26 |
| 16:1 cis 9 | 1.40–8.06 | 4.83 |
| 15:0 anteiso 2-hydroxyl | 1.35–8.68 | 3.12 |
| 16:0 | 1.41–6.39 | 5.17 |
| 16:0 9? methyl | 0.00–3.59 | 2.32 |
| 17:1 anteisi C | 1.01–4.30 | 3.76 |
| 17:0 iso | 0.00–2.04 | 1.81 |
| 17:0 anteiso | 1.11–7.08 | 7.50 |

TABLE 1-continued

Comparison of fatty acid profiles between Streptomyces strain NRRL B-16746 and that of the library entry for *Streptomyces albidoflavus*.

| Fatty Acid | S. albidoflavus Library Entry | Streptomyces sp. NRRL B-16746 |
|---|---|---|
| 17:1 cis 9 | 0.00–2.99 | 1.64 |
| 16:0 iso 2-hydroxyl | 0.00–6.85 | 0.00 |

*There was a 0.319 probability of matching *S. albidoflavus* using the ACTINO library supplied by MIDI, and a 0.764 probability of match using the in-house STMYB9 (Streptomyces Bergey's Manual, 9th Edition) library.

The strain was characterized as having olive-buff, smooth surfaced spores borne on flexuous sporophores and moderate yellowish-brown vegetative mycelium, was non-chromogenic, and utilized glucose, D-xylose, L-arabinose, D-fructose, D-galactose, raffinose, D-mannitol, inositol, salicin, and sucrose, but did not utilize L-rhamnose as sole carbon source. The strain was accessioned into the ARS Culture Collection (Peoria, Ill.) as NRRL B-16746.

The ability of streptomycetes to degrade chitin is well documented (Clarke, P. H., "The Occurrence of Chitinase in Some Bacteria," *J. Gen. Microbiol.*, 14:188–96 (1956), which is hereby incorporated by reference) and is characteristic of about 25% of the members of this genus (Williams, et al., "Numerical Classification of Streptomyces and Related Genera," *J. Gen. Microbiol.*, 129:1743–1813 (1983), which is hereby incorporated by reference). Streptomycetes have been shown to play a major role in degradation of chitin from fungal mycelium in acidic soil and litter (Williams, et al., "The Role of Streptomycetes in Decomposition of Chitin in Acidic Soils," *J. Gen. Microbiol.*, 127:55–63 (1981), which is hereby incorporated by reference).

Example 4

In Vitro Production of Alkaline Chitinolytic Enzymes

In general, secretion of fungal and bacterial chitinolytic enzymes is regulated by availability of carbon (e.g., chitodextrins); the presence of glucose or N-acetylglucosamine represses secretion of chitinolytic enzymes, while chitin induces the secretion of these enzymes (Harman, et al., "Chitinolytic Enzymes of *Trichoderma harzianum*: Purification of Chitobiase and Endochitinase," *Phytopathology*, 83:313–18 (1993), Monreal, et al., "The Chitinase of *Serratia Marcescens*," *Can. J. Microbiol.*, 15:689–96 (1969), St. Leger, et al., "Cuticle-Degrading Enzymes of Entomopathogenic Fungi: Regulation of Production of Chitinolytic Enzymes," *J. Gen. Microbiol.*, 132:1509–17 (1986), Ulhoa, et al., "Regulation of Chitinase Synthesis in *Trichoderma harzianum*," *J. Gen. Microbiol.*, 137:2163–69 (1991), which are hereby incorporated by reference). In support of these previous reports, the presence of chitin in the liquid medium resulted in a minimum of a 5-fold increase of all three types of enzyme activity secreted by *S. albidoflavus* (Table 2).

TABLE 2

The influence of chitin amendment on the level
of chitinolytic activity secreted by
Streptomyces albidoflavus NRRL B-16746.

| Broth* | Glucosaminidase % nkatals | | Chitobiosidase % nkatals | | Endochitinase Units/ml | |
|---|---|---|---|---|---|---|
| | pH 5 | pH 9 | pH 5 | pH 9 | pH 5 | pH 9 |
| + chitin | 87 ± 20 | 12 ± 9 | 51 ± 11 | 24 ± 18 | 79 | 43 ± 2 |
| − chitin | 16 ± 5 | 2 ± 1.6 | 7 ± 1 | 1 ± 0.5 | 0 | 0 |

*+ chitin indicates 0.5% chitin + 0.1% glucose in the standard growth medium; − chitin indicates 0.3% glucose and no chitin. Data are the average ± SE from three replicates.

Figure 1B:
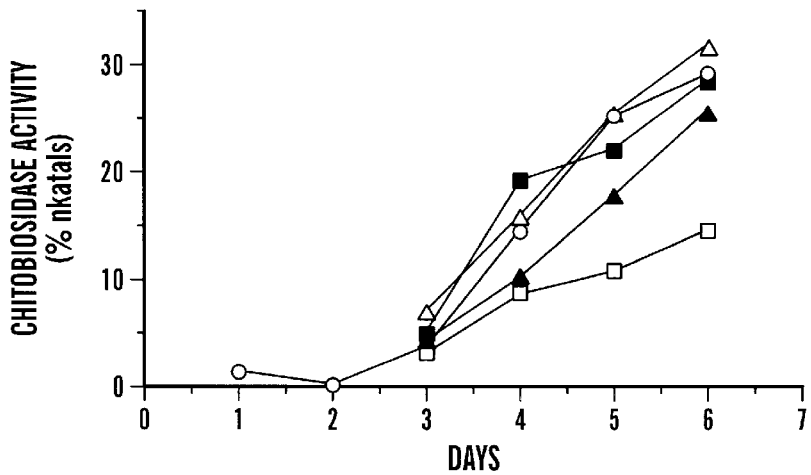
Figure 1C:
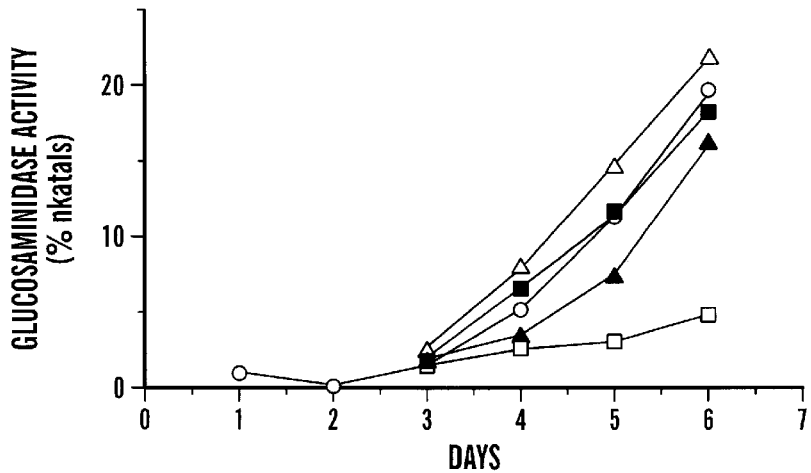

Based on these findings, chitin was added to the liquid medium to enhance the production of chitinolytic enzymes by S. albidoflavus NRRL B-16746. Addition of glucose also influenced the level of chitinolytic enzyme activity (FIG. 1); however, this was not always in the suppressive manner reported previously. After 6 days of culture, low levels of glucose (i.e., 0.01%) elevated the level of chitinolytic activity by 10–20%, while high levels of glucose (i.e., 0.5%) suppressed chitinolytic activity by 50–75%.

Figure 2A:
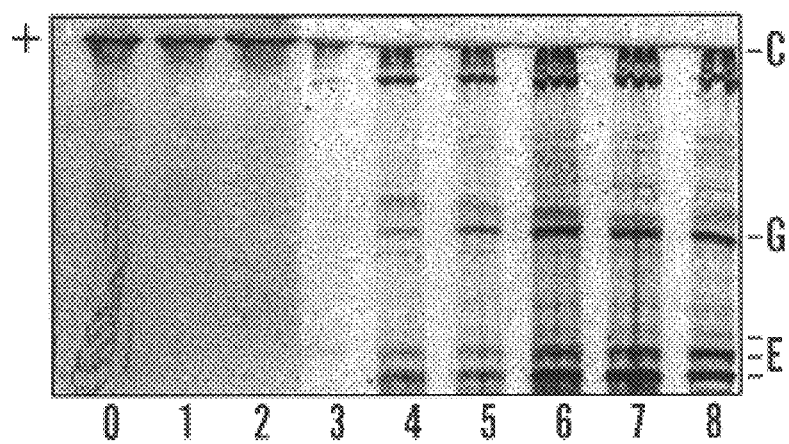
FIGS. 2A–B show the polyacrylamide gel electrophoresis of dialyzed culture filtrate from *Streptomyces albidoflavus* NRRL B-16746. Lanes 1–8 contain samples collected after 0, 24, 48, 72, 96, 120, 144, 168, or 192 hrs. of culture, respectively.
Figure 2B:
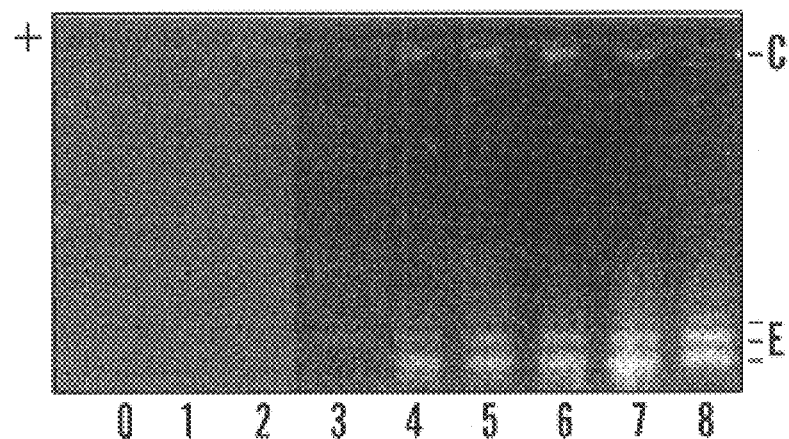

In conjunction with this latter study, the time course of production of chitinolytic enzymes by S. albidoflavus NRRL B-16746 was examined. Polyacrylamide gel electrophoresis ("PAGE") followed by Coomassie staining indicated that a limited number of proteins occurred in the broth during 8 days of culture (FIG. 2A). A comparison of this gel with PAGE followed by agar-overlay containing a chitinolytic enzyme-specific, fluorogenic substrate indicated that 50–75% of the protein in the broth had chitinolytic activity (FIG. 2B). Furthermore, comparison of the two gels (FIGS. 2A and B) indicated that the enzymes responsible for chitinolytic activity were differentially induced. The proteins with chitobiosidase and glucosaminidase activity were detectable at 96 hrs, while a single endochitinase was detectable after 72 hrs of culture, suggesting that the endochitinase was regulated independently from the other chitinolytic enzymes. Moreover, two additional endochitinases were detectable at 96 hrs, suggesting that these endochitinases may be regulated independently from each other. The more prominent of the two later endochitinases was larger and/or more basic than the first endochitinase, suggesting that these two proteins were encoded by different genes. The less prominent of the two later endochitinases was smaller and/or more acidic than the other two proteins. This third protein may have been the result of a third gene, or post-translational modification (e.g., proteolytic digestion) of the previous protein(s). In support of the latter possibility, proteolytic activity was detectable in the culture filtrate, and this enzyme activity was inhibited 45–70% by serine proteinase inhibitors.

Example 5

In vitro Analyses of Enzymatic Activity

Endochitinase activity was measured at pH 3–12, or pH 5 and pH 9. A 500 μl aliquot of sample was mixed with 500 μl 50 mM Tris pH 9, 0.1 M acetate buffer pH 5, or 0.1 M citrate-phosphate buffer pH 3–12 (for pH optimum study) containing 4% colloidal chitin. The mixture was shaken at 30 C for 24 hr. 5 ml of dH$_2$O was then added to each tube, vortexed, and the optical density was measured at 510 nm. Percent reduction of turbidity was calculated for each tube. For calculation of specific activity, one unit was defined as the amount of enzyme required to obtain 1% reduction of turbidity under the above conditions.

Chitobiosidase activity was measured at pH 3–12, or pH 5 and pH 9. A 30 μl aliquot of sample was transferred to a microtiter plate, and 50 μl of 50 mM Tris pH 9, 0.1 M acetate buffer pH 5, or 0.1 M citrate-phosphate buffer pH 3–12 (for pH optimum study) containing 0.03% p-nitrophenyl-D-N,N'-diacetylchitobiose was added to each well. The plate was incubated at 50 C for 15 min, then 50 μl of 0.4 M sodium carbonate was added to each well, and the optical density was measured at 410 nm. One nanokatal (nkatal) corresponds to the release of 1 nmol nitrophenyl×s$^{-1}$ under the above conditions. Data are reported as % nkatals (i.e., nkatals/100 ml).

Glucosaminidase activity was measured following the same procedure as that for chitobiosidase except the substrate was p-nitrophenyl N-acetyl-β-D-glucosaminide.

Prior to protein analyses, each fraction was dialyzed against dH$_2$O for 30 hr, to remove salts. Total protein was determined for each fraction using Coomassie stain reagent (Pierce Chemical Co., Rockford, Ill.). Chitinase from Serratia marcescens (Sigma Chemical Co., St. Louis, Mo.) was used as a standard.

Example 6 pH Range of Activity of Alkaline Chitinolytic Enzymes

Figure 3:
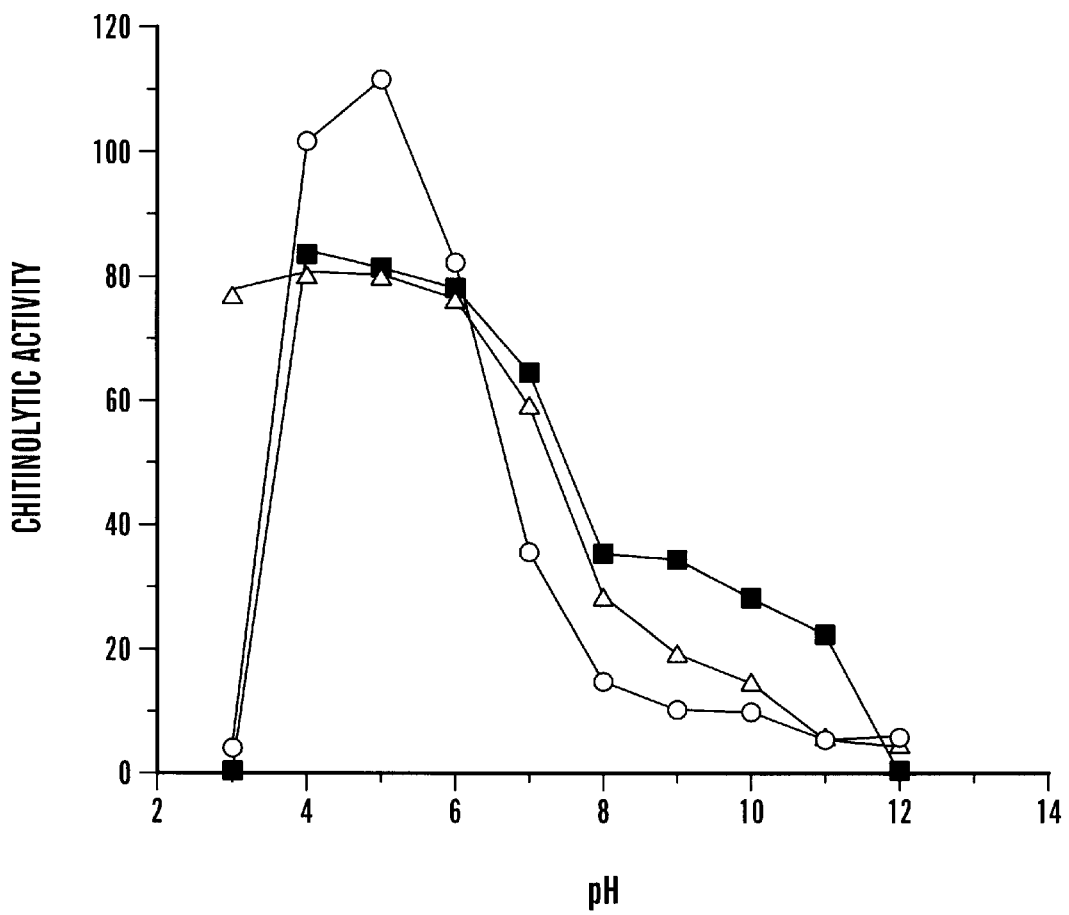
FIG. 3 shows the influence of pH on chitinolytic activity in the culture medium from *Streptomyces albidoflavus* NRRL B-16746. Glucosaminidase activity is indicated by the open circles, chitobiosidase activity is indicated by open triangles, and endochitinase activity is indicated by the solid squares.

Following 4–5 days of culture of S. albidoflavus in liquid medium containing chitin, the broth was filter-sterilized, dialyzed (MWCO12,000–14,000), and concentrated. This solution was used to determine the pH optimum for glucosaminidase, chitobiosidase, and endochitinase activity (FIG. 3). Although these enzymes had optimal activity at pH 4–6, there was significant endochitinase and chitobiosidase activity at pH 8–9. When comparing enzyme activity at pH 9 with activity at pH 5 from six different preparations of bacterial broth supernatant, only 6.8±1.6% of glucosaminidase activity was detectable at pH 9 compared to pH 5, while 54.5±9.7% of the chitobiosidase activity was detectable and 74.4±8.1% of the endochitinase activity was detectable. The chitinolytic enzymes from other species of Streptomyces retain activity in alkaline conditions; however, the level of activity at pH 9 generally is 10–40% of the activity at pH 5 (Hara et al., "Purification and Characterization of Chitinase Produced by Streptomyces erythraeus," J. Biochem., 105:484–89 (1989), Neugebauer, et al., "Chitinolytic Properties of Streptomyces lividans," Arch. Microbiol, 156:192–97 (1991), Tsujibo, et al., "Purification and Properties of Two Types of Chitinases Produced by an Alkalophilic Actinomycete," Biosci. Biotech. Biochem., 56:1304–05 (1992), Ueno, et al., "Purification and Some Properties of Extracellular Chitinases from Streptomyces sp. S-84," J. Gen. Appl. Microbiol., 36:377–92 (1990), Yabuki, et al., "Purification and Characterization of Chitinase and Chitobiase Produced by Aeromonas hydrophila subsp. anaerogenes A52," J. Gen. Anpl. Microbiol., 32:25–38 (1986), which are hereby incorporated by reference). An exception is a thermophilic bacteria, Streptomyces thermoviolaceus, that secretes an endochitinase that has optimal activity at pH 8–10. However, this enzyme activity requires an environmental temperature of 70–80 C (Tsujibo, et al., "Purification and Properties of a Thermostable Chitinase from Streptomyces thermoviolaceus OPC-520," Appl. Environ. Microbiol., 59:620–22 (1993), which is hereby incorporated by reference). Since chitinolytic enzymes that functioned in an alkaline environment were of interest, the chitobiosidases and endochitinases were characterized.

Example 7

Time Course of Enzyme Secretion

Liquid medium was prepared with either 0.3% glucose or 0.5% chitin+0%, 0.1%, 0.25%, or 0.5% glucose. A 10 ml aliquot was removed from the bacterial shaker flask every day for 8 days. On each day of collection, each sample was centrifuged and filtered, then each sample was adjusted to contain 0.02% sodium azide (anti-microbial agent). After all samples were collected, they were analyzed for enzyme activity. To prepare the samples for electrophoresis, they were dialyzed against $dH_2O$ to remove all salt, and concentrated in a speed-vac (Savant).

Example 8

Purification of Chitinolytic Enzymes

The strain of *Streptomyces albidoflavus* used for production of chitinolytic enzymes is accessioned in the ARS Culture Collection (Peoria, Ill.) as NRRL B-16746 (Broadway, et al., "Partial Characterization of Chitinolytic Enzymes from *Streptomyces albidoflavus*," *Lett. App. Microbiol.*, 20:271–76 (1995), which is hereby incorporated by reference). Chitinolytic enzymes were produced by *Streptomyces albidoflavus* when grown in liquid medium containing 0.012% magnesium sulfate, 0.1% glucose, 0.1% calcium chloride, 0.05% manganese sulfate, 0.025% ferrous sulfate, 0.00125% zinc sulfate, and 0.5% crab shell chitin in 50 mM Tris, pH 9.0. Cultures were grown in flasks with constant shaking (250 rpm) at 30 C for 4–5 days. The biomass was removed from the broth by centrifugation at 6000×g for 30 min, 4 C. The supernatant was filtered through mira cloth, then adjusted to 95% saturation with ammonium sulfate to isolate total protein. Ammonium sulfate precipitation enhanced the relative level of activity of the chitobiosidases and endochitinases, and reduced the level of glucosaminidase activity that was detectable at pH 9 (Table 3).

TABLE 3

| Broth* | Glucosaminidase % nkatals | | Chitobiosidase % nkatals | | Endochitinase Units/ml | |
|---|---|---|---|---|---|---|
| | pH 5 | pH 9 | pH 5 | pH 9 | pH 5 | pH 9 |
| Broth | 131 | 10 | 81 | 60 | 29 | 0 |
| AmmSO$_4$ precipitate | 63 | 5 | 81 | 75 | 41 | 23 |
| AmmSO$_4$ supernatant | 1 | 1 | 14 | 2 | 18 | 0 |

The ammonium sulfate ("AmmSO$_4$") precipitate was incubated at 4 C, overnight, then centrifuged at 6000×g for 30 min. at 4 C. The pellet was resuspended in $dH_2O$ and dialyzed against ice-cold $dH_2O$ (130×vol) to remove salt. The dialysate was centrifuged at 6000×g for 10 min, 4 C to remove insoluble particles, and the supernatant was lyophilized. This powder was identified as semipurified chitinolytic enzyme mixture.

Figure 4:
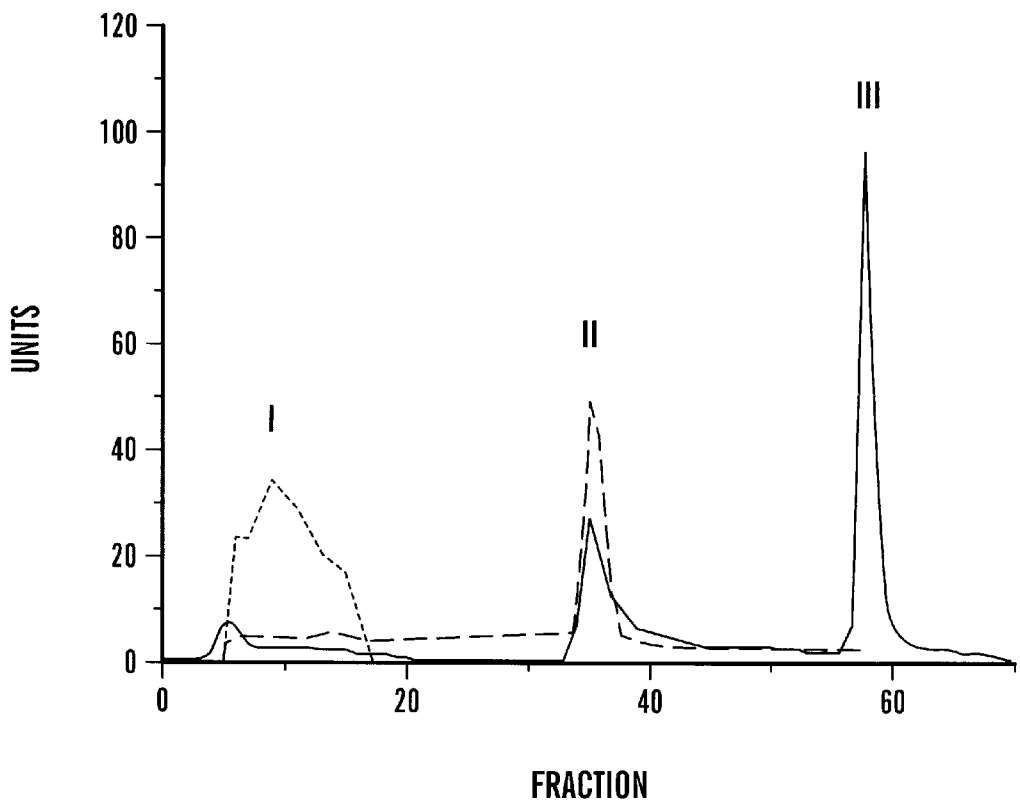
FIG. 4 shows the low pressure anion exchange chromatography of chitinolytic enzymes from *Streptomyces albidoflavus* NRRL B-16746. The solid line indicates total protein (optical density, 280 nm), the dashed line indicates chitobiosidase activity (% nkatals), and the dotted line indicates endochitinase activity (units/ml). These are representative data; the analysis was replicated more than 10 times.

A 50 mg sample of the lyophilized protein was resuspended in 100 mM Tris pH 8.5, then applied to a low pressure anion exchange column (16 cm×2.5 cm DEAE, Pharmacia) that was equilibrated with Tris buffer, pH 8.5. Fractions of 8 ml were collected (FIG. 4). Non-adsorbed material (peak I, which included endochitinases) was washed from the column with the Tris buffer until the optical density of the eluent approached zero. The chitobiosidases were then eluted with peak II with Tris buffer containing 0.2 M NaCl. The column was then cleaned with Tris buffer containing 1.0 M NaCl. The endochitinase (peak 1 from the DEAE column) was further purified by perfusion chromatography (BioCAD Sprint, Perceptive) on an HQ/M anion exchange column (4.6 mm×100 mm), equilibrated with 20 mM Tris/bis-Tris propane, pH 9.0. The sample was dialyzed against ice-cold $dH_2O$, then applied to the column; fractions of 2 ml were collected. Non-adsorbed material was washed from the column with buffer, then endochitinases were eluted with a gradient of sodium chloride (0 to 100 mM). The column was cleaned with buffer containing 1.0 M NaCl. Anion exchange chromatography purified the chitobiosidase 12.6×, and the endochitinase 13.5× (Table 4).

TABLE 4

Purification of chitinolytic enzymes in broth from *Streptomyces albidoflavus* NRRL B-16746. All enzyme assays were performed at pH 9.

| Purification Step | Total Activity (units) | Specific Activity (units/mg) Protein | Yield (%) | Purification Factor |
|---|---|---|---|---|
| Culture filtrate | | | | |
| chitobiosidase | 140 | 0.5 | 100 | 1.0 |
| endochitinase | 18,600 | 67 | 100 | 1.0 |
| Ammonium sulfate ppt | | | | |
| chitobiosidase | 137 | 1.2 | 98 | 2.4 |
| endochitinase | 7735 | 68 | 42 | 1.0 |
| DEAE Column | | | | |
| chitobiosidase | 107 | 6.3 | 76 | 12.6 |
| endochitinase | 9045 | 905 | 49 | 13.5 |

Figure 9:
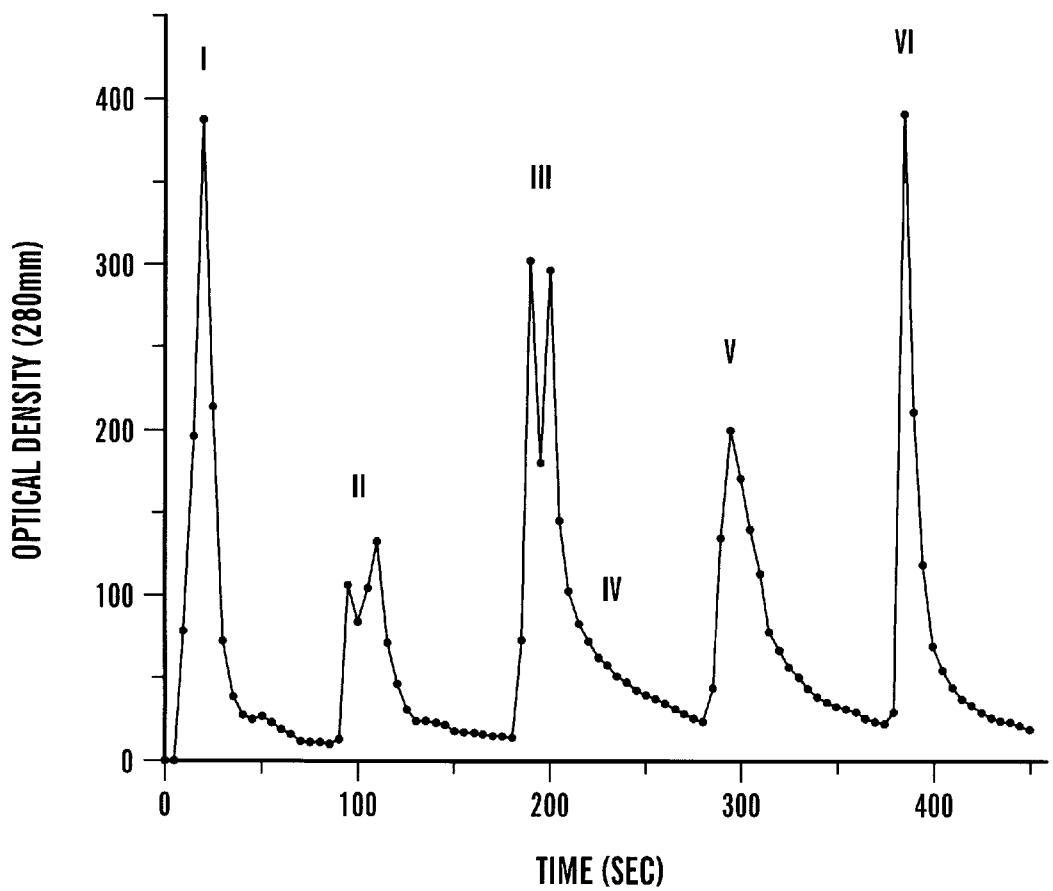
FIG. 9 shows the strong anion exchange perfusion chromatography of semipurified chitinolytic enzymes. Total chitinolytic activity, as measured by hydrolysis of p-nitrophenyl β-D-N,N'-diacetylchitobiose, was 0.14 nkat/peak I, 1.52 nkat/peak II, 0.26 nkat/peak III, <0.01 nkat/peak IV, 2.45 nkat/peak V, and 0.09 nkat/peak VI.
Figure 10A:
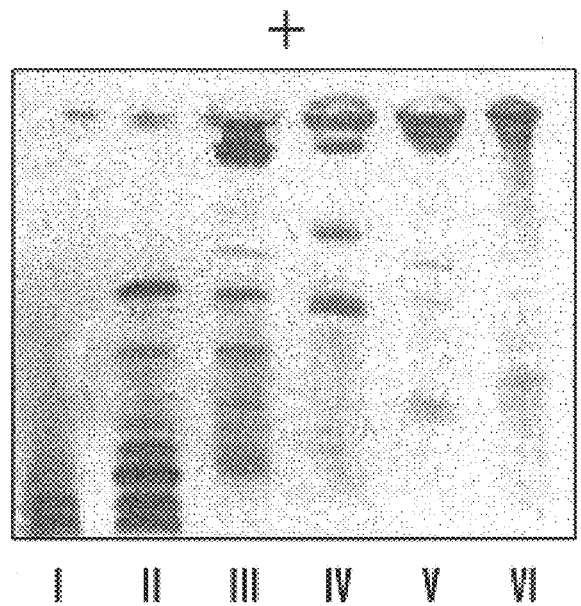
FIGS. 10A–B show polyacrylamide gel electrophoresis of the peaks collected from anion exchange perfusion chromatography (FIG. 9).
Figure 10B:
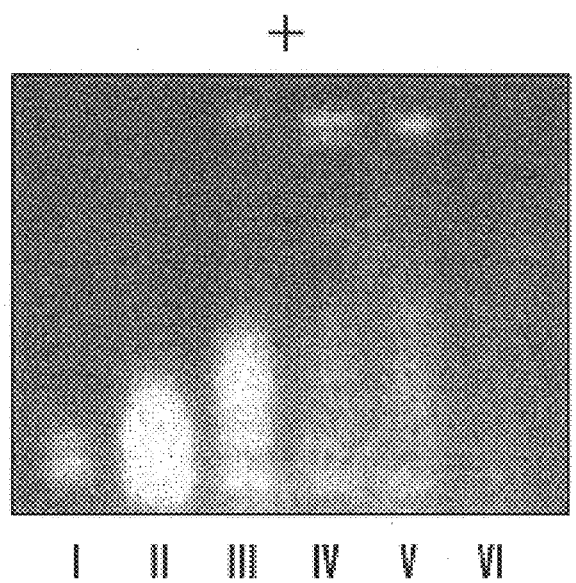

An alternative to the DEAE anion exchange chromatography for separating the endochitinases from the chitobiosidases in the ammonium sulfate precipitate is by the direct use of perfusion chromatography (BioCAD Sprint, PerSeptive Biosystems, Cambridge, Mass.) on an HG/M strong anion exchange column (4.6 mm×100 mm), equilibrated with 20 mM Tris/bis-Tris propane, pH 9.0. A 5 mg sample of chitinolytic enzyme mixture was applied to the column, and the endochitinases were separated from the chitobiosidases, as shown by the elution profile of the column (FIG. 9). The endochitinases were eluted as 2 protein peaks: peak I was eluted with the Tris buffer and peak II was eluted with 80 mM NaCl in Tris buffer. The chitobiosidases were eluted with 300 mM NaCl in Tris buffer. The column was cleaned with buffer containing 2 M NaCl. Samples were collected in 2 ml fractions; fractions were pooled to combine protein(s) from a single peak. Each peak of protein was dialyzed against ice-cold $dH_2O$, lyophilized, then analyzed for total protein and enzyme activity. The proteins were then applied to a non-denaturing polyacrylamide PhastGel (procedure described below) to confirm the presence of endochitinase(s) and/or chitobiosidase(s) (FIG. 10A). Based on these in vitro analyses, peaks I and II contained endochitinase activity, peaks IV and V had chitobiosidase activity, while peak III had endochitinase and chitobiosidase activity. Peak III was not used for bioassays against insects, because it contained both types of enzyme activity]. Peak VI had no chitinolytic activity (FIG. 10B).

Example 9

Polyacrylamide Gel Electrophoretic Analyses of Chitinolytic Enzymes

The PhastSystem electrophoresis unit (Pharmacia, Uppsala, Sweden) was used to characterize the proteins with chitinolytic activity. The number of proteins with chitinolytic activity was determined on a non-denaturing, discontinuous polyacrylamide gel (7.5% stacking gel, 20% separating gel, separation length 32 mm), using non-denaturing buffer strips containing 0.88 M L-alanine, 0.25 M Tris, pH 8.8. A 3 µl aliquot of the sample was mixed with 1 µl 4×sample buffer (0.25 M Tris, pH 8.8, 0.008% bromophenol blue (w/v)), then transferred to a sample applicator for electrophoresis.

The molecular weights were determined on 0.45 mm discontinuous, polyacrylamide PhastGel consisting of a 20% polyacrylamide separating gel and a 7.5% polyacrylamide stacking gel with a separating length of 32 mm. The buffer strips contained 0.2 M Tricine, 0.2 M Tris, 0.55% SDS, pH 8.1. A 3 µl aliquot of the sample was mixed with 1 µl 4× sample buffer (40 mM Tris, 4 mM EDTA, pH 8.0, 10% SDS, 20% β-mercaptoethanol, 0.04% bromophenol blue (w/v)), then placed in boiling water for 30 sec, centrifuged for 15 sec, and transferred to a sample applicator for electrophoresis. The molecular weight markers (BioRad) included soybean trypsin inhibitor (21.5 kD), carbonic anhydrase (31 kD), ovalbumin (45 kD), bovine serum albumin (66.2 kD), and phosphorylase B (97.4 kD).

Isoelectric points were determined on a 0.35 mm 5% polyacrylamide PhastGel containing ampholytes for pI 4 to 6.5 with a total separation length of 37 mm. A 4 µl aliquot of each sample was analyzed. A mixture of isoelectric focusing markers (Sigma) included methyl red marker dye (pI 3.8), amyloglucosidase (pI 3.6), soybean trypsin inhibitor (pI 4.6), bovine beta-lactoglobulin A (pI 5.1), carbonic anhydrase II (pI 5.9), carbonic anhydrase I (pI 6.6), horse myoglobin (pI 6.8 and 7.2), L-lactic dehydrogenase (pI 8.3, 8.4, and 8.6), and bovine trypsinogen (pI 9.3).

All protein bands were visualized by staining the polyacrylamide gel with Coomassie (0.1% Coomassie R350 in 30% MeOH, 10% acetic acid). Proteins with chitobiosidase and endochitinase activity were detected on gels with an overlay containing 0.025% 4-methylumbelliferyl β-D-N,N'-diacetylchitobioside in 0.05 M Tris pH 9, 1% low melting DNA-grade agarose. Glucosaminidase activity was detected on polyacrylamide gels with an overlay containing 0.025% 4-methylumbelliferyl-N-acetyl-β-D-glucosaminide. The agarose-based mixture was boiled for 5 min, then cooled to 35 C. Immediately following electrophoresis, the agarose mixture was poured over the gel, and the fluorescent bands were visualized with UV light.

Polyacrylamide gel electrophoresis ("PAGE") followed by Coomassie staining indicated that the broth from *Streptomyces albidoflavus* contained a limited number of proteins. PAGE followed by agar-overlay of an enzyme-specific, fluorogenic substrate (Harman, et al., "Chitinolytic Enzymes of *Trichoderma harzianum*: Purification of Chitobiase and Endochitinase," *Phytopathology*, 83:313–18 (1993), which is hereby incorporated by reference) indicated that 50–75% of the proteins in the broth had chitinolytic activity (Broadway, et al., "Partial Characterization of Chitinolytic Enzymes from *Streptomyces albidoflavus*," *Lett. Appl. Microbiol.*, 20:271–76 (1995), which is hereby incorporated by reference).

Figure 5A:
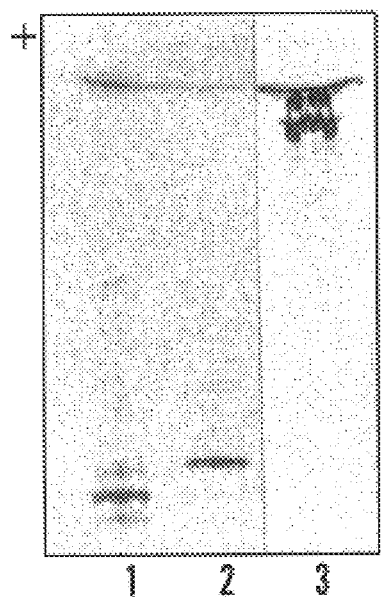
FIGS. 5A–B show the polyacrylamide gel electrophoresis of chitinolytic enzymes from anion exchange chromatography. Lanes 1 and 2 contain endochitinases (peaks III and IV, respectively, from FIG. 8), and lane 3 contains chitobiosidases (peak II from FIG. 4). The gels were stained with Coomassie (FIG. 5A), or a chitinase-specific fluorogenic substrate (FIG. 5B). These are representative data; the determination of the number of chitinolytic enzymes was replicated more than 10 times.
Figure 5B:
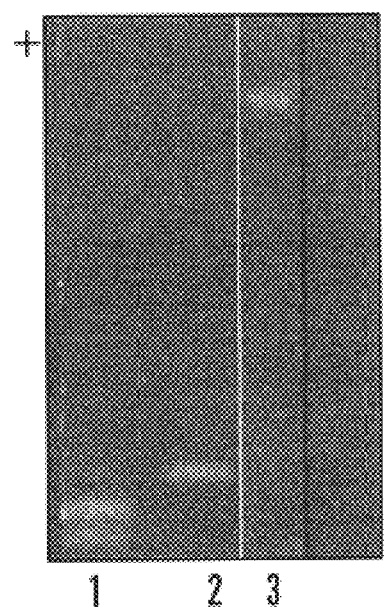
Figure 6A:
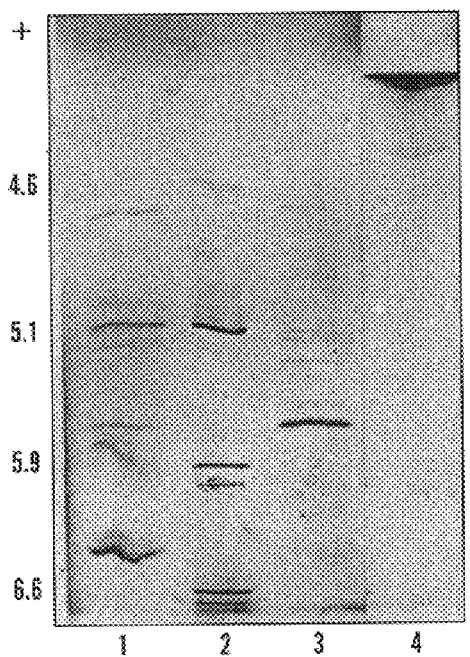
FIGS. 6A–B show the isoelectric focusing gel of chitinolytic enzymes from anion exchange chromatography. The gels were stained with Coomassie (FIG. 6A), or a chitinase-specific fluorogenic substrate (FIG. 6B). For FIG. 6A, lane 1 contains endochitinases (peaks III from FIG. 8), lane 2 contains isoelectric focusing markers, lane 3 contains endochitinases (peaks IV from FIG. 8), and lane 4 contains chitobiosidases (peak II from FIG. 4). For FIG. 6B, lane 1 contains endochitinases (peaks IV from FIG. 8), lane 2 contains endochitinases (peaks III from FIG. 8), and lane 3 contains chitobiosidases (peak II from FIG. 4). The isoelectric points of the chitobiosidases were <3.0, while the isoelectric points of the endochitinases were 6.4, 5.8–5.9, 5.7, 5.3, 5.1, and 5.0. These are representative data; the isoelectric point determinations were replicated more than 10 times.
Figure 6B:
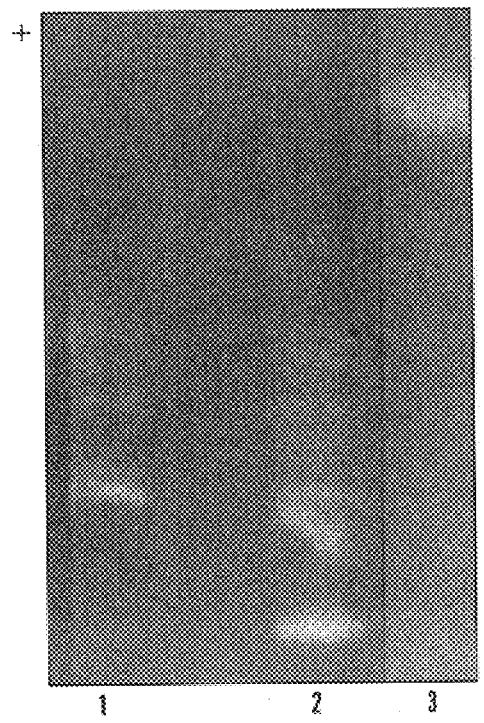
Figure 7:
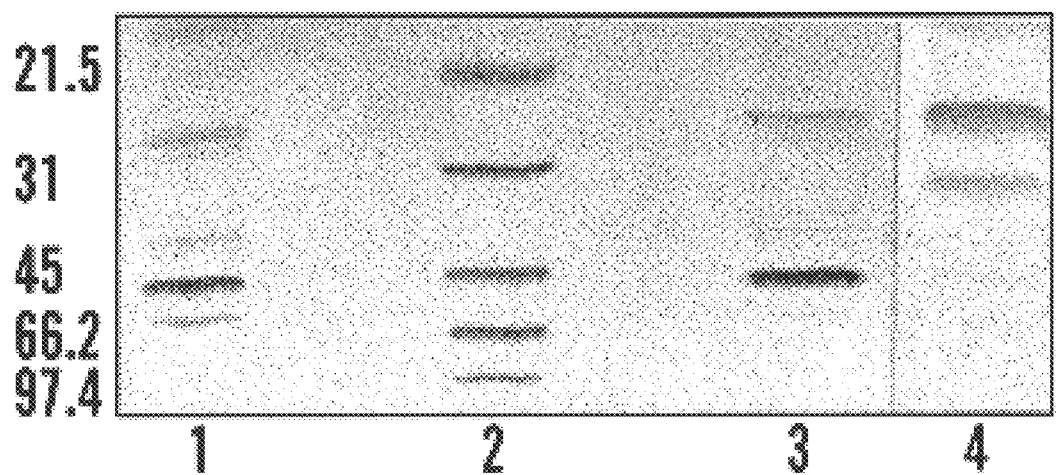
FIG. 7 shows the SDS-polyacrylamide gel electrophoresis of chitinolytic enzymes from anion exchange chromatography. Lane 1 contains endochitinases (peak III from FIG. 8), lane 2 contains molecular weight markers, lane 3 contains endochitinases (peak IV from FIG. 8), lane 4 contains chitobiosidases (peak II, FIG. 4). The gel was stained with Coomassie. The proteins with chitobiosidase activity have molecular mass of 59, 45, 38.5, 27, and 25.5 kD. These are representative data; the molecular weight determinations were replicated more than 10 times.
Figure 8:
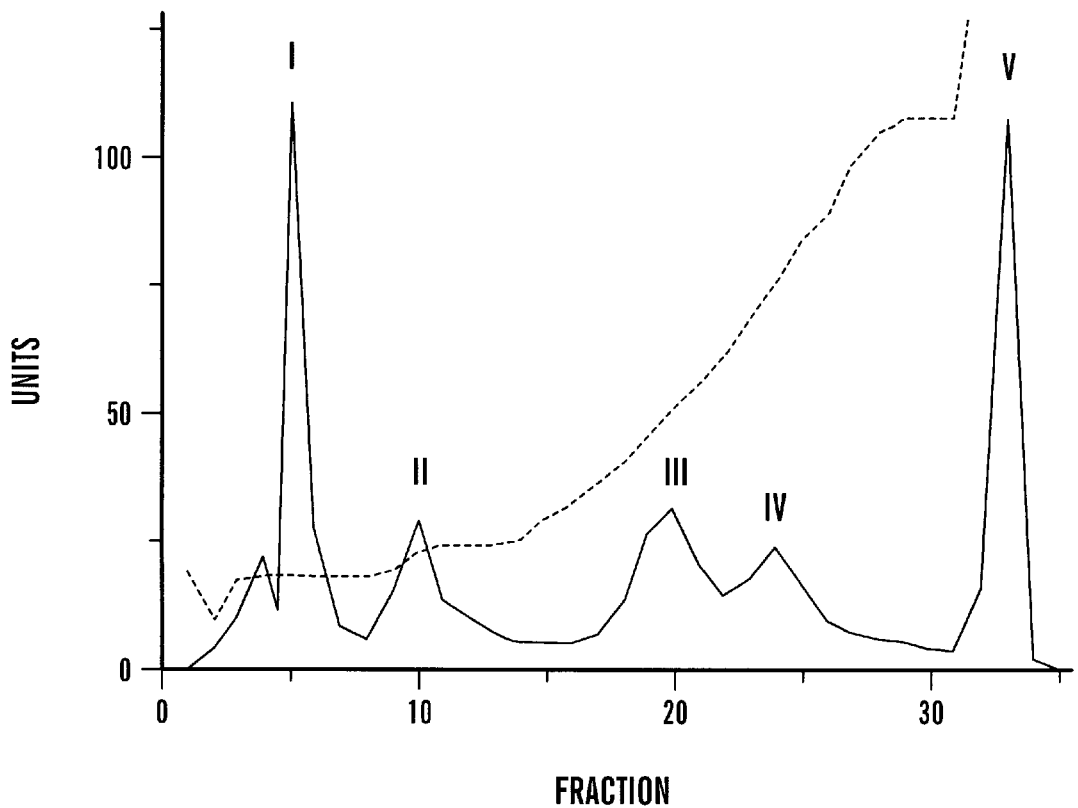
FIG. 8 shows the perfusion anion exchange chromatography of endochitinases (FIG. 4, peak I) from *Streptomyces albidoflavus* NRRL B-16746. The solid line indicates total protein (optical density, 280 nm), the dashed line indicates sodium chloride gradient. Endochitinase activity occurred in peaks III and IV. These are representative data; the chromatographic separation was replicated 6 times.

Each protein peak from the DEAE column was dialyzed against dH$_2$O, then concentrated 10× in a speed-vac (Savant) prior to electrophoretic analyses. PAGE of the proteins in peak II indicated that the chitobiosidase activity originated from two proteins (FIG. 5) with isoelectric points 3.0 (FIG. 6), and molecular weights of 27 and 34 kD (FIG. 7). Perfusion chromatography of the endochitinases (peak I from DEAE) removed contaminating proteins. Endochitinase activity occurred in peaks III and IV (FIG. 8). PAGE of the proteins in these two peaks indicated that the endochitinase activity originated from 5 major proteins (FIG. 5) with isoelectric points of 5.1, 5.3, 5.75, 5.8–5.9, and 6.4 (FIG. 6), and a minor protein at pI 5.0. The molecular mass of the 5 major endochitinases were 59, 45, 38.5, 27, and 25.5 kD (FIG. 7). This study demonstrates that the chitinolytic enzymes from *S. albidoflavus* NRRL B-16746 have activity at the pH that occurs in the guts of herbivorous insects, and are small enough to allow molecular transformation of agricultural crops.

Example 10

Glycosylation

A glycan detection kit (Boehringer Mannheim, Indianapolis, Ind.) was used to determine whether the chitinolytic enzymes were glycosylated. In brief, the proteins were oxidized with periodate, then incubated with digoxigenin, which binds to oxidized sugar moieties. The mixture was electrophoresed on SDS-PAGE, transferred to nitrocellulose, then incubated with anti-digoxigenin antibody, which is conjugated to alkaline phosphatase. The antibody-glycoprotein complexes were visualized calorimetrically.

Digoxigenin glycan analysis (Boehringer Mannheim Biochemica) indicated that the chitinolytic enzymes were not glycosylated.

Example 11

Amino Acid Analysis

Amino acid analyses were performed at the Cornell Amino Acid Facility on the Waters Pico-Tag HPLC System (Cohen et al. "Analysis of Amino Acids Using Pre-column Derivatization with Phenylisothiocyanate," *Amer. Lab*, (1984), which is hereby incorporated by reference). Samples were concentrated, then the endochitinases were separated by native-PAGE, and the chitobiosidases were separated by SDS-PAGE. The proteins were electrophoretically transferred to PVDF transfer membrane (Immobilon-P, 0.45 µm, Millipore) using the PhastSystem Transfer Unit and Tris/glycine transfer buffer (25 mM Tris, 192 mM glycine, pH 8.5, 20% MeOH). The Immobilon was stained with Coomassie (0.1% Coomassie, 60% MeOH, 7.5% acetic acid), destained with 75% MeOH, 7.5% acetic acid, then exhaustively rinsed with double distilled H$_2$O to remove excess glycine originating from the transfer buffer. Each protein band was acid hydrolyzed (6N HCl, 115 min, 150, under partial vacuum and N$_2$), the amino acids were extracted from the Immobilon, then analyzed for amino acid composition (Cohen et al. "Analysis of Amino Acids Using Pre-column Derivatization with Phenylisothiocyanate," *Amer. Lab*, (1984), which is hereby incorporated by reference).

Amino acid analysis was performed on the two chitobiosidase proteins and three of the endochitinase proteins (Table 5).

TABLE 5

Amino acid analysis of five chitinolytic enzymes from *Streptomyces albidoflavis* NRRL B-16746.

| Amino Acid | Chitobiosidases | | Endochitinases | | |
|---|---|---|---|---|---|
| | A<br>34 kD | B<br>27.5 kD | C<br>pI 6.4<br>% pmol | D<br>pI 5.75 | E<br>pI 5.3 |
| ASX | 13 | 12 | 9 | 10 | 9 |
| GLX | 9 | 9 | 5 | 5 | 5 |
| HIS | 1 | 4 | 2 | 2 | 2 |
| ARG | 3 | 4 | 3 | 3 | 4 |
| LYS | 3 | 2 | 7 | 7 | 5 |
| SER | 6 | 7 | 6 | 6 | 7 |
| GLY | 11 | 14 | 13 | 13 | 13 |
| THR | 8 | 7 | 9 | 9 | 10 |
| TYR | 4 | 5 | 5 | 5 | 4 |
| CYS | 0 | 1 | 1 | 0 | 1 |
| MET | 2 | 1 | 1 | 1 | 1 |
| ALA | 14 | 10 | 15 | 14 | 16 |
| PRO | 4 | 6 | 5 | 5 | 6 |
| VAL | 7 | 5 | 5 | 5 | 7 |
| ILE | 3 | 3 | 4 | 3 | 4 |
| LEU | 8 | 7 | 6 | 6 | 6 |
| PHE | 4 | 5 | 5 | 5 | 4 |

The chitinolytic enzymes had 40.6±1.4% pmol of hydrophobic amino acids, indicating that these enzymes were not membrane proteins (membrane-bound proteins contain more than 30–40% hydrophobic amino acids), and they contained 7–12% pmol of basic amino acids, which is comparable to generalized proteins (Reeck, G. "Proteins" in *CRC Handbook of Biochemistry and Moleuclar Biology*, pp. 504–511, Edited by G. D. Fasman. Cleveland: CRC Press (1976), which is hereby incorporated by reference). However, the chitobiosidases had a high level of acidic amino acids (i.e., 21–22%) compared to the endochitinases (14–15% acidic amino acids), which accounts for the strongly acidic isoelectric point of the chitobiosidases.

Example 12

Insects

To determine the effect of chitinolytic enzymes on the growth and development of Lepidoptera, larval *Trichoplusia ni* (cabbage looper) were reared on a high wheat germ-based meridic diet (Webb et al., "Laboratory Rearing of the Imported Cabbageworm," *NY Food Life Sci. Bull.,* 122 (1988), which is hereby incorporated by reference) supplemented with chitinolytic enzymes. Each bioassay included 4 treatments (0, 0.25%, 0.5%, and 1% of chitinolytic enzyme mixture), 3 cups/treatment, 20 neonate larvae/cup, and each bioassay was replicated three times. All larvae were weighed when controls reached the ultimate instar and then monitored daily for developmental changes. The percent pupation and percent adult emergence was based on the total number of larvae weighed and total number of pupae recovered from each test diet, respectively.

Larvae of the Coleoptera *Hypothenemus hampei* (coffee berry borer) were maintained individually in wells of an ELISA plate, each well containing 0.2 ml of artificial diet (Villacorta et al., "Nova Dieta Meridica Para Criacao De *Hypothenemus hampei* (Ferrari) (Coleoptera: Scolytidae)," *A. Soc. Entom. Brasil,* 22:405–09 (1993), which is hereby incorporated by reference). Incubation conditions were maintained at 26 C, 60–70% relative humidity. Each bioassay included 4 treatments (0, 0.25%, 0.5%, and 1% chitinolytic enzyme mixture), 20 eggs/treatment, and each bioassay was replicated three times. The insects were monitored during 30 days for developmental changes (from egg to adult) and mortality.

The Homoptera *Myzus persicae* (green peach aphid) was reared on turnip plants prior to use in experiments. Each bioassay consisted of 6 treatments (0%, 0.06%, 0.125%, 0.25%, 0.5%, and 1% chitinolytic enzyme mixture prepared in 20% sucrose), replicated four times each. Immature wingless aphids of similar age, were each placed in a glass cylinder arena (22 mm inner diameter, 21 mm height) covered on one end with parafilm. The other end of the arena was sealed when placed upright on a supporting substrate. An aliquot of 20% sucrose solution was added to the top of the parafilm, and another piece of parafilm stretched over the solution to form a thin layer of solution. The parafilm provided a membrane through which aphids could feed. Aphids were held for 24 hrs. in the cylinders to become acclimated to the test arena. After 24 hours, the number of surviving aphids was recorded, the parafilm was replaced, and the sucrose solution was replaced with experimental chitinase solutions. Percent mortality was recorded at 24 and 48 hrs. after the chitinase solutions were added.

Adult whiteflies, *Bemisia argentifolii,* of similar age were obtained by placing poinsettia leaves infested with pupae from the colony into sleeve cages provisioned with a poinsettia plant. Adults were allowed to emerge from pupae for one day before the remaining pupae were removed to prevent further adult emergence. Adults were then left in the cage on the poinsettia plant for an additional two days before use. Bioassays were conducted within polycarbonate vials (45 mm diameter, 74 mm height) over which parafilm was thinly stretched. A 0.5 ml aliquot of 10% sucrose solution, with or without chitinolytic enzymes, was placed onto the parafilm and covered by another tightly stretched layer of parafilm as with aphid trials. Twenty adult whiteflies were released into each vial through a small hole in the side of the vial and periodically evaluated for mortality over 3 d. Bioassays included a control treatment (10% sucrose) and either semipurified chitinase at 0.06, 0.125, 0.25, 0.5, and 1.0%, or one of five chitinase fractions at 0.5%. Each treatment was replicated three to six times for each bioassay. Aphid and whitefly trials were conducted on a laboratory bench under conditions of 12L:12D and 22C.

Example 13

Biological Activity of Alkaline Chitinolytic enzymes Against Insects

In vitro analyses indicated that chitinolytic enzymes will digest the peritrophic membrane from larval Lepidoptera. In addition, there was no loss of chitinolytic activity when the contents within the midgut lumen from larval Lepidoptera (*Trichoplusia ni* or *Pieris rapae*) was incubated for 60 min with a crude mixture of chitinolytic enzymes from *Streptomyces albidoflavus,* indicating that the bacterial chitinolytic enzymes were not susceptible to proteolytic digestion by the enzymes in the midgut lumen of larval *T. ni* and *Pieris rapae.* Also, chitinolytic enzymes did not lose activity when incorporated into an artificial diet and maintained in an environmental chamber for 5 days, or when ingested by larval *T. ni,* indicating that the enzymes could be incorporated into an artificial diet for biological testing, and that insects did not secrete an inhibitor of chitinolytic enzymes when there was chitinolytic activity in the gut. More importantly, a mixture of chitobiosidases and endochitinases (extracted from the bacterial culture filtrate by ammonium sulfate precipitate, then dialyzed, and lyophilized) significantly reduced the growth and/or survival of herbivorous insects (as shown below).

Figure 11:
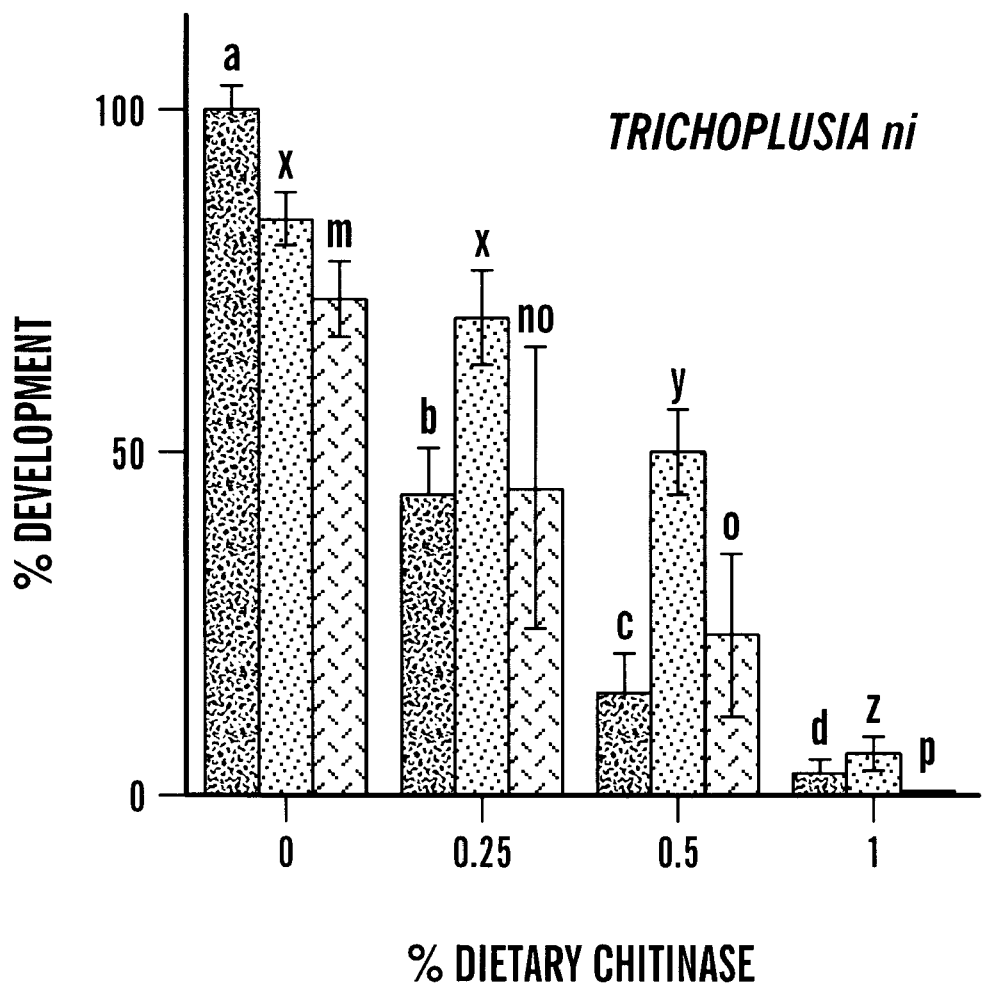
FIG. 11 shows the development of *Trichoplusia ni* larvae on artificial diet supplemented with semipurified chitinolytic enzymes. Solid bars indicate larval weight as a percent of the mean weight of untreated controls. Stippled bars indicate the percent larvae that pupated. Hatched bars indicate the percent pupae that molted to adults. Vertical lines indicate ±1 SEM. Columns associated with an insect growth stage having similar letters are not significantly different (LSD test).

The lyophilized, chitinolytic enzyme mixture contained 0.8 to 1.1 nkat of chitobiosidase activity/mg, and 154 to 165 units of endochitinase activity/mg. Dietary supplementation with the mixture of enzymes resulted in significant reductions in larval weight (expressed as percentage of the control) (F=121.56, df=3,23, P=0.0001), % pupation (F=34.69, df=3,20, P=0.0001), and % adult emergence (F=6.64, df=3,8, P=0.015) for *Trichoplusia ni* (FIG. 11).

Figure 12A:
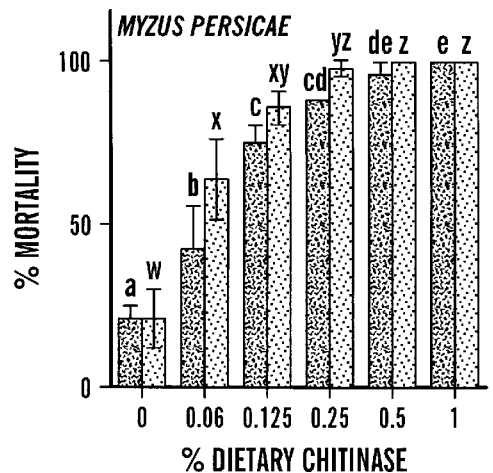
FIG. 12 shows the effect of dietary chitinolytic enzymes on survival of *Myzus persicae, Bemisia argentifolii,* and *Hypothenemus hampei*. For *B. argentifolii,* solid bars indicate % mortality after 18 h exposure, stippled bars indicate % mortality after 42 h exposure. For *M. persicae,* solid bars indicate % mortality after 24 h exposure, while stippled bars indicate % mortality after 48 h exposure. For *H. hampei,* solid bars indicate % mortality after 30d exposure. Vertical lines indicate ±1 SEM. Columns associated with a single time of observation and having similar letters are not significantly different (LSD test).
Figure 12B:
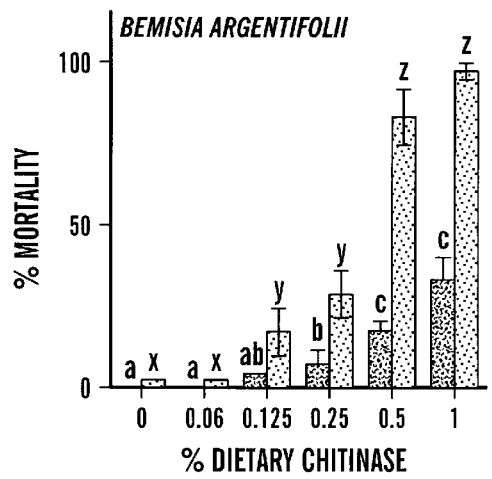
Figure 12C:
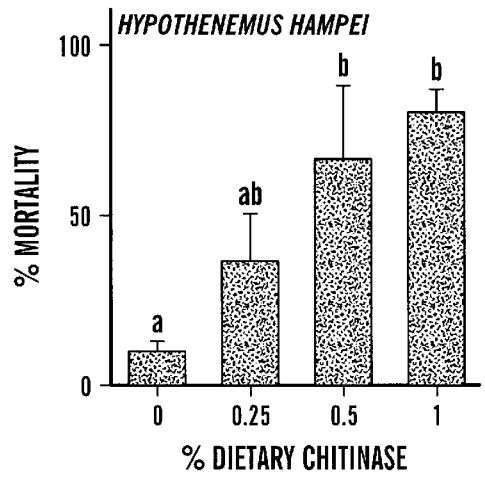
Figure 13:
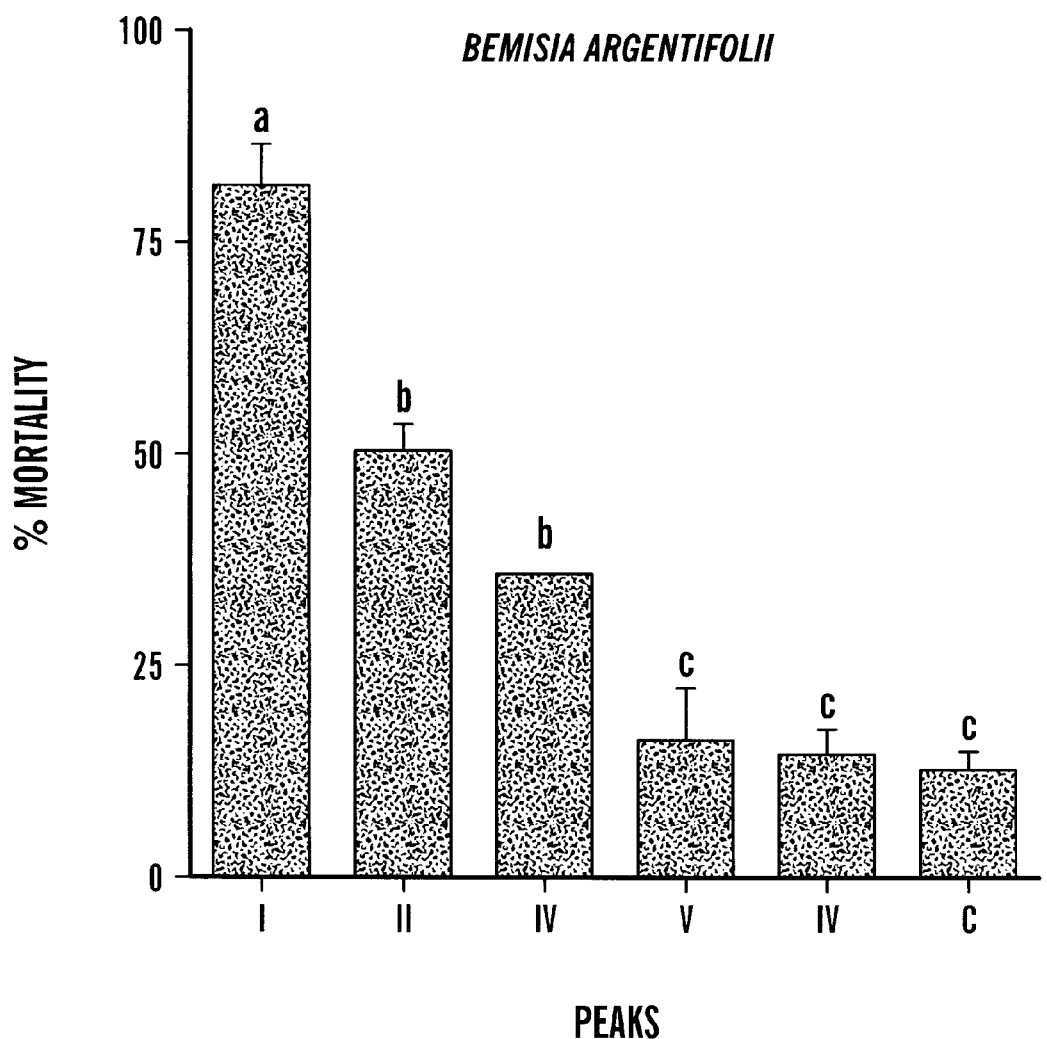
FIG. 13 shows the effect of dietary endochitinases or chitobiosidases on survival of *Bemisia argentifolii*. Endochitinase treatments I and II contained 10% sucrose and 0.5% peak I or II, respectively, from the anion exchange perfusion chromatography (FIG. 9), while chitobiosidase treatments IV and V contained 10% sucrose and 0.5% peak IV or V, respectively, from the anion exchange column (FIG. 9). Two controls were included: treatment VI contained 10% sucrose and 0.5% peak VI (no chitinolytic activity), and treatment C, which contained 10% sucrose. Vertical lines indicate ±1 SEM. Columns with similar letters are not significantly different (LSD test).
Figure 14:
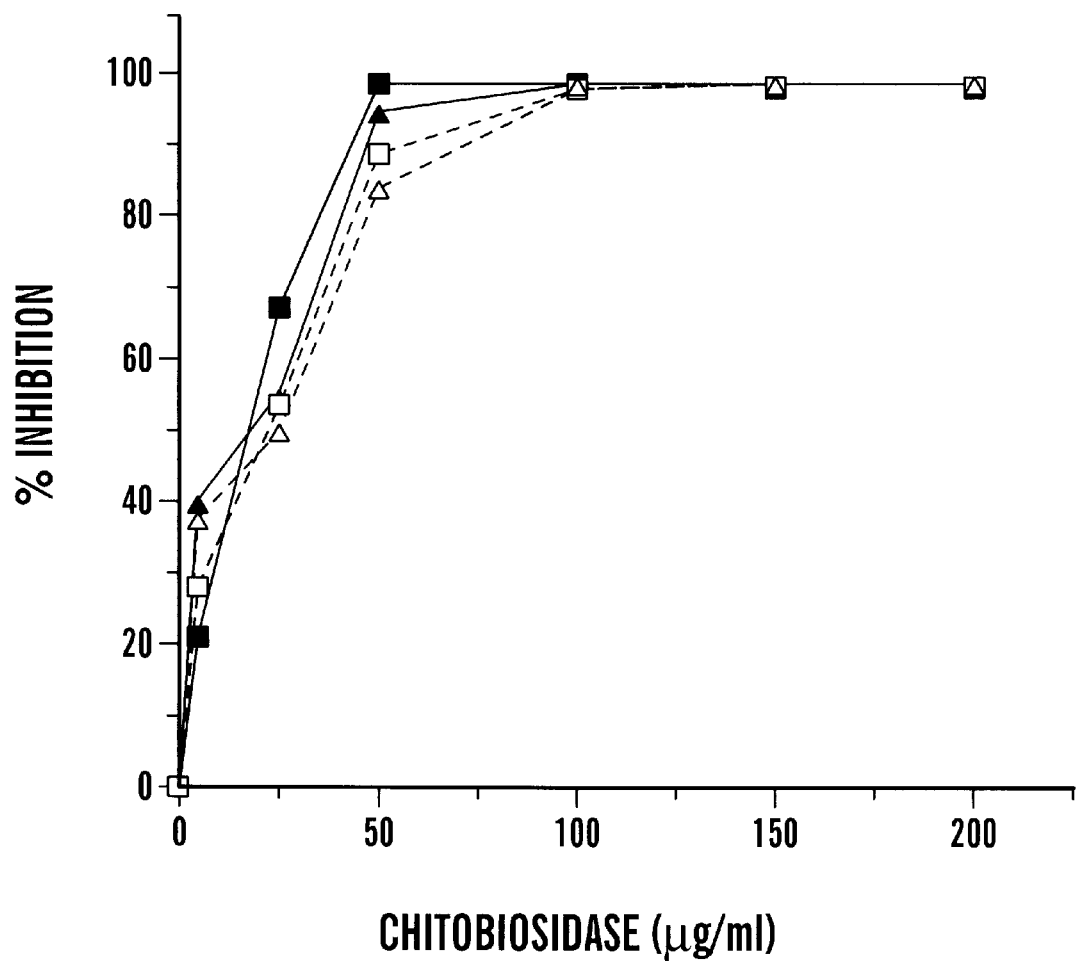
FIG. 14 shows the biological activity of chitobiosidases against *Botrytis cinerea* and *Fusarium oxysporum*. Square indicates % inhibition of spore germination, triangle indicates % inhibition of germ tube elongation, dashed line indicates *Botrytis cinerea,* and solid line indicates *Fusarium oxysporum*.

In addition, ingestion of the mixture of chitinolytic enzymes resulted in a dose-dependent increase in mortality for *Myzus persicae* at 24 and 48 hrs. (F=20.33 and 20.02, respectively; df=5,15, P=0.0001), *Bemisia argentifolii* at 18 and 42 hr. (F=11.23 and 25.12, respectively; df=5,11,P 0.0005) and *Hypothenemus hampei* (F=5.84, df=3,8, P=0.021) at 30d (FIG. 12).

Separation of endochitinases from chitobiosidases resulted in significantly different levels of mortality for adult *B. argentifolii* (F=17.77, df=5,19, P=0.0001). Fractions containing endochitinase (peaks I and II) resulted in 80 and 50%O mortality, respectively, after 36 hr. of exposure. The fraction containing both proteins with chitobiosidase activity (peak IV) significantly elevated mortality to 38%, whereas mortality following exposure to a single (most acidic) chitobiosidase (peak V) did not differ from the untreated controls (Peak VI and C) (FIG. 13).

The current study demonstrated that ingestion of an artificial diet containing a mixture of endochitinases and chitobiosidases will significantly reduce the growth and development of larval *Trichoplusia ni* (FIG. 11) and significantly decrease the survival of *Myzus persicae, Bemisia argentifolii,* and *Hypothenemus hampei* (FIG. 12). Separation of the endochitinases from the chitobiosidases was accomplished by perfusion chromatography (FIGS. 9 and 10). Feeding studies indicated that the endochitinases dramatically reduced survival of *Bemisia argentifolii* (which may have been due to acute toxicity or repellency following ingestion), while the chitobiosidases had less of an effect on survival. These results are in contrast to previous work that demonstrated that the chitobiosidases from *Streptomyces albidoflavus* significantly reduced the growth and survival of the plant pathogenic fungi *Botrytis cinerea* and *Fusarium oxysporum* (Broadway, et al., "Partial Characterization of Chitinolytic Enzymes from *Streptomyces albidoflavus,*" *Lett. Appl. Microbiol.,* 20:271–76 (1995), which is hereby incorporated by reference).

The results of this study provided fundamental information required for evaluating the impact of chitinolytic enzymes on the growth and/or development of herbivorous insects.

Example 14

Biological Activity of Chitinolytic Enzymes against Fungi

Bioassays (following the methods of Lorito, M., Harman, G. E., Hayes, C. K., Broadway, R. M., Tronsmo, A., Woo, S. L. and DiPietro, A., "Chitinolytic Enzymes Produced by *Trichoderma harzianum:* Antifungal Activity of Purified Endochitinase and Chitobiase," *Phytopathology* 83:302–07 (1993), which is hereby incorporated by reference) indicated that the purified chitobiosidases significantly reduced spore germination and germ tube elongation for *Botrytis cinerea* ($ED_{50}$=16 $\mu$g/ml) and *Fusarium oxysporum* ($ED_{50}$=18–26 $\mu$g/ml) (See FIG. 14).

Example 15

Isolation of Genes that Encode Chitinolytic Enzymes from *S. albidoflavus*

The amino-terminal sequence of a chitobiosidase (i.e., with a molecular mass of 31 kD and isoelectric point of 3.9) and an endochitinase (i.e., with an isoelectric point of 6.3 and molecular mass of 41.6 kD) was determined at the Analytical Chemistry Facility, Cornell Biotechnology Program. Degenerate oligonucleotides were synthesized at the Oligonucleotide Synthesis Facility, Cornell Biotechnology Program and at the Entomology Department, using departmental facilities, based on the N-terminal sequences of the endochitinase and chitobiosidase proteins. Additional oligonucleotides were synthesized based on endochitinase homology region 2 (Hayes, et al., "Isolation and sequence of an endochitinase gene from a cDNA library of *Trichoderma harzianum,*" *Gene,* 135:143–148 (1994), which is hereby incorporated by reference), and a conserved region found from a comparison of exochitinases from *S. lividans* and *S. olivaceoviridis.*

Genomic DNA was extracted from an overnight culture of bacteria grown in trypticase soy broth using standard techniques (Hopwood, et al., *Genetic Manipulation of Streptomyces: A Laboratory Manual,* John Innes Foundation, Norwich (1985), which is hereby incorporated by reference). The DNA was partially digested with Sau3AI, ligated to LambdaGem-11 BamHI arms (Promega), and packaged with Gigapack II extract (Stratagene).

Oligonucleotides specific to the endochitinase (N-terminal and homology region 2 oligonucleotides) were used in PCR to amplify a portion of the endochitinase gene from bacterial genomic DNA. A prominent band of approximately 400 base pairs was detected after gel electrophoresis of PCR products. This band was electroeluted and sequenced directly using dye labelled terminators, thermal cycling, and an ABI automatic sequencer according to the manufacturer's instructions. A peptide sequence derived from this DNA from *S. albidoflavus* had 90% identity with an endochitinase protein sequence from *S. plicatus* (Robbins, et al., "Cloning and High-Level Expression of Chitinase-Encoding Gene of *Streptomyces plicatus,*" *Gene,* 111:69–76 (1992), which is hereby incorporated by reference), indicating that a fragment of an endochitinase gene from *S. albidoflavus* was isolated. This fragment was used to screen the genomic library. Several clones were plaque-purified and all were found to contain the same hybridizing SalI fragments. The 1,500 bp of a phage clone were sequenced. This region contained a potential open reading frame of 311 amino acids which had 79% identity to the endochitinase of *S. plicatus.* Each gene was subcloned and their individual sequences were determined.

The chitobiosidase-specific oligonucleotides (N-terminal and exochitinase homology) were used in PCR to amplify a portion of the chitobiosidase gene. A fragment of about 220 bp was electroeluted, sequenced, and used to screen the genomic library as described above. A 4.5 kbp NotI-XhoI fragment was subcloned from a plaque-purified phage clone into pBS and sequenced. This fragment contained a potential open reading frame with a peptide sequence of 74% identity to an exochitinase from *S. lividans.*

Bacterial genomic DNA was digested with one of several enzymes and analyzed by genomic Southern blotting. Several hybridizing bands in each restriction digest were present on blots probed at reduced stringency with the endochitinase PCR fragment. The endochitinases of *S. albidoflavus* are believed to be members of a small family of 3–4 genes. At least two of these endochitinase genes have been cloned.

On blots probed at reduced stringency with the chitobiosidase PCR product, a unique band was seen in all digests. This suggests that the cloned chitobiosidase has a unique gene. As reported above, two distinct chitobiosidase proteins were seen on protein gels. Two proteins could be produced from the same gene by post-translational modification of a single peptide, or the two proteins and their genes may be closely related. The N-terminal sequence of the second chitobiosidase protein was determined. The sequence obtained was distinct from the cloned chitobiosidase.

The cloned chitinase genes were expressed in *E. coli* to obtain pure, individual proteins to produce antibodies against chitinases. Chitobiosidase expression in *E. coli* was obtained using the pTrcHis vector (Invitrogen). PCR was used to amplify the chitobiosidase gene and to introduce appropriate flanking restriction sites. Features of the pTrcHis expression system are (1) IPTG-inducible, high level expression, (2) a strong repressor, and (3) the recombinant protein is expressed as a fusion with 6 histidine residues and a short linker. The 6×His residues allow for rapid affinity selection on nickel containing resins (Ni-NTA, Quagen) with mild elution conditions (low pH or imidazole competition) and the linker contains an enterokinase cleavage site to remove the 6×His tail.

The chitobiosidase gene was expressed at high levels in *E. coli*. Induced, overnight cultures contained equivalent chitobiosidase activity as 5 day chitin-induced cultures of *S. albidoflavus*. Recombinant chitobiosidase binds strongly to the Ni-NTA resin and is effectively eluted at a pH of 5.5.

The same protocol was followed to produce recombinant endochitinases.

Example 16

Transgenic Tomato Plants

Three binary plasmids were constructed, and Agrobacterium-mediated plant transformation was chosen to carry out tomato and apple transformation. Target genes were cloned into binary plasmid under the control of appropriate promotors. The following plasmids were constructed for this purpose:

Biase19: One *S. albidoflavus* chitobiosidase gene was amplified by PCR and put under control of a double CaMV 35S promoter and a nopoline synthase terminator (i.e. NPTII) in the expression vector pBin19.

Endo19: One *S. albidoflavus* endochitinase gene was amplified by PCR and put under the control of a double CaMV 35S promoter and a nopoline synthase terminator in the expression vector pBin19.

BiaseEndo19: The chitobiosidase gene and the endochitinase gene are both put under the control of a double CaMV 35S promoter and a nopoline synthase terminator, respectively, then tandemly ligated in the expression vector pBin19.

*Agrobacterium tumefaciens* strain LBA4404 was successfully transformed with all three constructs using electroporation.

Four tomato strains were used for transformation. A processing tomato (*Lycopersicon esculentum*, UC82B) was selected for initial transformation, because it is commercially used by the tomato industry. However, UC82B is a slow growing variety, significantly prolonging the transformation process. Two fast growing strains (Better Boy VFN and Beefmaster VFN) were later transformed. In addition, another strain, Geneva80 was also transformed, because it was locally developed and successfully transformed with other genes.

All three constructs were used to transform the plants. However, emphasis was placed on the double construct BiaseEndo19, and most of the transgenic plants were generated using this construct. Transformants included:

53 transgenic UC82B tomato plants from 27 lines;

15 transgenic Beefmaster tomato plants from 11 lines;

3 transgenic Better Boy tomato plants from 3 lines; and 11 transgenic Geneva80 tomato plants from 8 lines.

Antibodies were raised against both the chitobiosidases and endochitinases.

ELISA assays were used to test the expression of NTPII gene, the Biase gene, and the Endo gene. At least 20 UC82B plants, 9 Beefmaster plants, and 1 Better Boy plant are expressing high level of NPTII: 25 UC82B plants, 12 Beefmaster plants, 2 Better Boy plants, and 5 Geneva80 plants are expressing the Biase gene. The expression level of Biase is low in most of the plants, but at least 4 plants (UC.BE2.A1, UC.BE3.A8, UCBE4.H3, BM.BE1.K1) are expressing a relatively high level of Biase.

Chitin is a target site that distinguishes arthropods from higher organisms. Chitin is a principle component of the insect's exoskeleton (which includes the foregut and hindgut) and peritrophic membrane (which surrounds the midgut), and is essential for structural integrity of insects. Digestion of chitin located in the digestive tract (i.e., foregut, hindgut, and/or peritrophic membrane) may significantly disrupt nutrient acquisition, digestion, and/or absorption, along with other protective and/or physiological functions. For example, the peritrophic membrane is thought to function as (1) protection against abrasion of the gut wall (the site of absorption and some digestion), (2) compartmentalization of digestion in the midgut lumen, and (3) a barrier to pathogens and phytotoxins. Destruction of the peritrophic membrane should have a negative impact on all three of these functions that are essential for the survival of insects. Ingestion of an artificial diet containing a mixture of chitinolytic enzymes will significantly reduce the growth and/or development of *Trichoplusia ni*, and survival of *Myzus persicae, Hypothenemus hampei*, and *Bemisia tabaci*. In addition, chitinolytic enzymes function within the midgut fluid and will digest the peritrophic membrane, in vitro.

Plants are known to contain chitinolytic enzymes that function as an effective phytochemical defense against plant pathogens. There are no reports in the literature to indicate that researchers have examined the effect of plant chitinolytic enzymes on herbivorous insects. However, plant chitinolytic enzymes may have no biological activity against herbivorous insects due to the pH requirements of these enzymes. Plant chitinolytic enzymes, in general, require an acidic environment for activity. They have little or no activity in an alkaline environment. However, herbivorous insects, in general, have alkaline midguts (Berenbaum, M., "Adaptive Significance of Midgut pH in Larval Lepidoptera," *Amer. Natural.*, 115:138–46 (1980); Grayson, J. M., "Acidity-Alkalinity in the Alimentary Canal of Twenty Insect Species," *Virginia J. Sci., Jan:*46–59 (1951); Mishra, et al., "pH Trends in the Gut of Xylophagous Insects and Their Adaptive Significance," *Mater. Organ.*, 22:311–19 (1987), which are hereby incorporated by reference). Therefore, chitinolytic enzymes from plants probably have no activity within the lumen of the insect gut. Another source of chitinolytic enzymes is insects which use the enzymes to digest chitin during the moulting process. However, insects also produce factors that will regulate the production and activity of these enzymes, which may interfere with use of these proteins. Therefore, bacteria or other microbes may be the most appropriate source of chitinolytic enzymes for use against insects.

Example 17

Transformation of Tomato or Apple Plants with Gene for Chitinolytic Enzymes Enhances Resistance to Insects Bioassays were conducted according to the procedures of Broadway, et al., "Influence of Cabbage Proteinase Inhibitors in situ on the Growth of Larval Trichoplusia and *Pieris rapae*," *J. Chem. Ecol.*, 18:1009–024 (1992), which is hereby incorporated by reference. The following results were achieved.

Larval *Heliocoverpa virescens* are significantly smaller when they feed on Macintosh apple plantlets that were transformed with the gene for chitobiosidase than when they feed on non-transformed (control) Macintosh plantlets [average larval weight: 289 mg (transformed plants) vs 385 mg (control plants)].

Larval *Trichoplusia ni* are significantly smaller when they feed on Beefmaster tomato that has been transformed with the chitobiosidase+endochitinase genes than when they feed on non-transformed (control) Beefmaster tomato [average larval weight: 30 mg (transformed plants) vs 143 mg (control plants)].

Tomato plants that were transformed with the chitobiosidase+endochitinase genes showed significantly less feeding damage by larval *Trichoplusia ni* than control plants [relative level of feeding damage: 2% (transformed plants) vs 45% (control plants)].

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated DNA molecule encoding a *Streptomyces albidoflavus* chitinolytic enzyme having chitinolytic activity under alkaline conditions.

2. An isolated DNA molecule according to claim 1, wherein the chitinolytic enzyme is selected from the group consisting of chitobiosidase and endochitinase.

3. An isolated DNA molecule according to claim 2, wherein the chitinolytic enzyme is chitobiosidase.

4. An isolated DNA molecule according to claim 3, wherein the chitobiosidase has a molecular mass of 34 kD and an isoelectric point of less than 3.0.

5. An isolated DNA molecule according to claim 3, wherein the chitobiosidase has an amino acid sequence comprising SEQ. ID. No. 1.

6. An isolated DNA molecule according to claim 2, wherein the chitinolytic enzyme is an endochitinase.

7. An isolated DNA molecule according to claim 6, wherein the endochitinase has a molecular mass of 45 kD and an isoelectric point of about 6.5.

8. An isolated DNA molecule according to claim 6, wherein the endochitinase has an amino acid sequence comprising SEQ. ID. No. 3.

9. An expression system transformed with the DNA molecule according to claim 1.

10. An expression system according to claim 9, wherein the chitinolytic enzyme is selected from the group consisting of chitobiosidase, endochitinase, and combinations thereof.

11. An expression system according to claim 9, wherein the DNA molecule is in proper sense orientation and correct reading frame.

12. A host cell transformed with the DNA molecule according to claim 1.

13. A host cell according to claim 12, wherein the chitinolytic enzyme is selected from the group consisting of chitobiosidase, endochitinase, and combinations thereof.

14. A host cell according to claim 12, wherein the host cell is a bacterial cell.

15. A host cell according to claim 12, wherein the host cell is a plant cell.

16. A host cell according to claim 12, wherein the host cell contains an expression system transformed with the DNA molecule.

17. A transgenic plant transformed with the DNA molecule according to claim 1.

18. A transgenic plant according to claim 17, wherein the chitinolytic enzyme is selected from the group consisting of chitobiosidase, endochitinase, and combinations thereof.

19. A transgenic plant according to claim 18, wherein the chitinolytic enzyme is chitobiosidase.

20. A transgenic plant according to claim 18, wherein the chitinolytic enzyme is an endochitinase.

21. A transgenic plant according to claim 17, wherein the plant is selected from the group consisting of Gramineae, Liliaceae, Iridaceae, Orchidaceae, Salicaceae, Ranunculaceae, Magnoliaceae, Cruciferae, Rosaceae, Leguminosae. Malvaceae, Umbelliferae, Labitatae, Solanaceae, Cucurbitaceae, Compositae, and Rubiaceae.

22. A transgenic plant seed transformed with the DNA molecule according to claim 1.

23. A transgenic plant seed according to claim 22, wherein the chitinolytic enzyme is selected from the group consisting of chitobiosidase, endochitinase, and combinations thereof.

24. A transgenic plant seed according to claim 22, wherein the plant seed is selected from the group consisting of Gramineae, Liliaceae, Iridaceae, Orchidaceae, Salicaceae, Ranunculaceae, Magnoliaceae, Cruciferae, Rosaceae, Leguminosae, Malvaceae, Umbelliferae, Labitatae, Solanaceae, Cucurbitaceae, Compositae, and Rubiaceae.

25. A method of insect control for plants comprising:
providing a transgenic plant or plant seeds transformed with a DNA molecule according to claim 1 and
growing the transgenic plant or transgenic plants produced from the transgenic plant seeds under conditions effective to control insects.

26. A method according to claim 25, wherein a transgenic plant is provided.

27. A method according to claim 25, wherein a transgenic plant seed is provided.

28. An isolated DNA molecule encoding a chitinolytic enzyme having chitinolytic activity under alkaline conditions, wherein said DNA molecule has a nucleotide sequence of SEQ. ID. Nos. 2 or 4 or a nucleotide sequence which hybridizes to the nucleotide sequence of SEQ. ID. Nos. 2 or 4 under stringent conditions.

29. An isolated DNA molecule according to claim 28, wherein the DNA molecule has a nucleotide sequence which hybridizes to the nucleotide sequence of SEQ. ID. Nos. 2 or 4 under stringent conditions.

30. An isolated DNA molecule according to claim 29, wherein the stringent conditions are 65° C. for 20 hours in a medium containing 1M NaCl, 50 mM Tris-HCl, pH 7.4, 10 mM EDTA, 0.1% sodium dodecyl sulfate, 0.2% ficoll 0.2% polyvinylpyrrolidone, 0.2% bovine serum albumin, 50 μm g/ml $E.\ coli$ DNA.

31. An expression system transformed with the DNA molecule according to claim 28.

32. A host cell transformed with the DNA molecule according to claim 28.

33. A host cell according to claim 32, wherein the host cell is a bacterial cell.

34. A host cell according to claim 32, wherein the host cell is a plant cell.

35. A host cell according to claim 32, wherein the host cell contains an expression system transformed with the DNA molecule.

36. A transgenic plant transformed with the DNA molecule according to claim 28.

37. A transgenic plant according to claim 35, wherein the plant is selected from the group consisting of Gramineae, Liliaceae, Iridaceae, Orchidaceae, Salicaceae, Ranunculaceae, Magnoliaceae, Cruciferae, Rosaceae, Leguminosae, Malvaceae, Umbelliferae, Labitatae, Solanaceae, Cucurbitaceae, Compositae, and Rubiaceae.

38. A transgenic plant seed transformed with the DNA molecule according to claim 28.

39. A transgenic plant seed according to claim 38, wherein the plant seed is selected from the group consisting of Gramineae, Liliaceae, Iridaceae, Orchidaceae, Salicaceae, Ranunculaceae, Magnoliaceae, Cruciferae, Rosaceae, Leguminosae, Malvaceae. Umbelliferae, Labitatae, Solanaceae, Cucurbitaceae, Compositae, and Rubiaceae.

40. A method of insect control for plants comprising:
providing a transgenic plant or plant seeds transformed with a DNA molecule according to claim 28 and
growing the transgenic plant or transgenic plants produced from the transgenic plant seeds under conditions effective to control insects.

41. A method according to claim 40, wherein a transgenic plant is provided.

42. A method according to claim 40, wherein a transgenic plant seed is provided.

43. A DNA molecule according to claim 1, wherein the chitinoltic enzyme has chitinolytic activity only under alkaline conditions.

44. A DNA molecule according to claim 28, wherein the chitinolytic enzyme has chitinolytic activity only under alkaline conditions.

45. An isolated DNA molecule according to claim 29, wherein the DNA molecule has a nucleotide sequence which hybridizes to the nucleotide sequence of SEQ. ID. No. 2 under stringent conditions.

46. An isolated DNA molecule according to claim 29, wherein the DNA molecule has a nucleotide sequence which hybridizes to the nucleotide sequence of SEQ. ID. No. 4 under stringent conditions.

47. An isolated DNA molecule according to claim 28, wherein the DNA molecule has a nucleotide sequence of SEQ. ID. No. 2.

48. An isolated DNA molecule according to claim 28, wherein the DNA molecule has a nucleotide sequence of SEQ. ID. No. 4.

* * * * *

UNITED STATES PATENT AND TRADEMARK OFFICE
Certificate

Patent No. 6,069,299                                              Patented: May 30, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Roxanne M. Broadway, Phelps; Gary E. Harman, Geneva; Both of N.Y.; and David L. Williams, Normal, IL.

Signed and Sealed this Fourteenth day of January 2003.

AMY J. NELSON
*Supervisory Patent Examiner*
Art Unit 1638

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 298 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:1:

```
Ala Pro Ala Ala Val Pro Ala His Ala Val Thr Gly Tyr Trp Gln Asn
 1               5                  10                  15

Phe Asn Asn Gly Ala Thr Val Gln Thr Leu Ala Asp Val Pro Asp Ala
             20                  25                  30

Tyr Asp Ile Ile Ala Val Ser Phe Ala Asp Ala Thr Ala Asn Ala Gly
         35                  40                  45

Glu Ile Thr Phe Thr Leu Asp Ser Val Gly Leu Gly Gly Tyr Thr Asp
     50                  55                      60

Glu Gln Phe Arg Ala Asp Leu Ala Ala Lys Gln Ala Asp Gly Lys Ser
65                  70                  75                  80

Val Ile Ile Ser Val Gly Gly Glu Lys Gly Ala Val Ala Val Asn Asp
                 85                  90                  95

Ser Ala Ser Ala Gln Arg Phe Ala Asp Ser Thr Tyr Ala Leu Met Glu
                100                 105                 110

Glu Tyr Gly Phe Asp Gly Val Asp Ile Asp Leu Glu Asn Gly Leu Asn
            115                 120                 125

Ser Thr Tyr Met Thr Glu Ala Leu Thr Lys Leu His Glu Lys Ala Gly
        130                 135                 140

Asp Gly Leu Val Leu Thr Met Ala Pro Gln Thr Ile Asp Met Gln Ser
145                 150                 155                 160

Pro Glu Asn Glu Tyr Phe Lys Thr Ala Leu Val Thr Lys Asp Phe Leu
```

```
                    165                 170                 175
Thr Ala Val Asn Met Gln Tyr Tyr Asn Ser Gly Ser Met Leu Gly Cys
                180                 185                 190

Asp Gly Gln Val Tyr Ala Gln Gly Thr Val Asp Phe Leu Thr Ala Leu
        195                 200                 205

Ala Cys Ile Gln Leu Glu Asn Gly Leu Asp Ala Ser Gln Val Gly Ile
    210                 215                 220

Gly Val Pro Ala Ser Pro Lys Ala Gly Gly Tyr Val Glu Pro
225                 230                 235                 240

Ser Val Val Asn Asp Ala Leu Asp Cys Leu Thr Arg Gly Thr Gly Cys
                245                 250                 255

Gly Ser Phe Lys Pro Glu Lys Thr Tyr Pro Ala Leu Arg Gly Ala Met
            260                 265                 270

Thr Trp Ser Thr Asn Trp Asp Ala Asp Thr Gly Asn Ala Trp Ser Asn
            275                 280                 285

Val Val Gly Pro His Val Asp Asp Leu Pro
290                 295

(2) INFORMATION FOR SEQ ID NO:2:

(i) SEQUENCE CHARACTERISTICS:
        (A) LENGTH: 1294 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

GCGGCCGCTC CGGGCGGACG ACCGTACGGA CTCCTCGGCC GACCCCTGCG GGAACCCTTG      60

ACAACCCCAT TGGTCTGGAC CAGTTTGGTG CCCATCGCGG TGGCCACCGT GCGCCAACTC     120

CCCGCCCCCT CCCGGGTGGC GGGCCCCGTC GGCGCGTCCC CCACGTCCG TGACTCCCCC      180

CACCGGAGGC AGCAGTGGTA CGCACCTACC CCCTTCCGCA CCCCGGCCGG CGCCCCTCCA    240

CGCCCGGCCT CCACCGCAGG GGCCGGCTGA CCGCCGCCCT CACCGCGGCC GTCCTCGGCG    300

CCTCCGGGCT CGCCCTCACC GGCCCCGCGA CCGCCGGCGA GGGGGCCCCC GCCGCCCAGG    360

CCGCCCCGGC CGCCGTACCG GCCCACGCGG TGACCGGTTA CTGGCAGAAC TTCAACAACG    420

GCGCGACCGT GCAGACCCTC GCCGACGTGC CGGACGCCTA CGACATCATC GCCGTCTCCT    480

TCGCCGACGC CACGGCCAAC GCGGGCGAGA TCACCTTCAC CCTCGACTCG GTCGGGCTCG    540

GCGGCTACAC CGACGAGCAG TTCCGCGCCG ACCTCGCCGC CAAGCAGGCC GACGGCAAGT    600

CGGTGATCAT CTCGGTCGGC GGCGAGAAGG GCGCGGTCGC CGTCAACGAC AGCGCCTCCG    660

CCCAGCGCTT CGCCGACAGC ACCTACGCGC TGATGGAGGA GTACGGCTTC GACGGCGTCG    720

ACATCGACCT GGAGAACGGC CTCAACTCCA CCTACATGAC CGAGGCCCTC ACCAAGCTCC    780

ACGAGAAGGC CGGGGACGGC CTGGTCCTCA CCATGGCGCC GCAGACCATC GACATGCAGT    840

CGCCCGAGAA CGAGTACTTC AAGACGGCGC TGGTCACGAA AGACTTCCTG ACCGCCGTCA    900

ACATGCAGTA CTACAACAGC GGCTCGATGC TCGGCTGCGA CGGCCAGGTC TACGCGCAGG    960

GCACCGTCGA CTTCCTCACC GCGCTCGCCT GCATCCAGCT GGAGAACGGT CTCGACGCCT   1020

CCCAGGTCGG CATCGGTGTC CCCGCCTCCC CGAAGGCGGC CGGCGGCGGC TACGTCGAGC   1080

CCTCCGTGGT CAACGACGCG CTGGACTGCC TGACCCGGGG CACCGGTTGT GGCTCGTTCA   1140

AGCCGGAGAA GACCTACCCG GCGCTGCGTG GCGCCATGAC CTGGTCGACC AACTGGGACG   1200
```

```
CCGACACCGG CAACGCCTGG TCGAACGTGG TCGGCCCGCA CGTCGACGAC CTGCCGTAAC    1260

CCCGGAGCCG GGCACCCGTC CGCTTCCCCC GCAC                                1294
```

(2) INFORMATION FOR SEQ ID NO:3:

(i) SEQUENCE CHARACTERISTICS:
        (A) LENGTH: 376 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

```
Gly Pro Gly Pro Gly Pro Arg Glu Lys Ile Asn Leu Gly Tyr Phe Thr
1               5                   10                  15

Glu Trp Gly Val Tyr Gly Arg Asn Tyr His Val Lys Asn Leu Val Thr
            20                  25                  30

Ser Gly Ser Ala Glu Lys Ile Thr His Ile Asn Tyr Ser Phe Gly Asn
        35                  40                  45

Val Gln Gly Gly Lys Cys Thr Ile Gly Asp Ser Phe Ala Ala Tyr Asp
    50                  55                  60

Lys Ala Tyr Thr Ala Ala Glu Ser Val Asp Gly Val Ala Asp Thr Trp
65                  70                  75                  80

Asp Gln Pro Leu Arg Gly Asn Phe Asn Gln Leu Arg Lys Leu Lys Ala
                85                  90                  95

Lys Tyr Pro His Ile Lys Val Leu Trp Ser Phe Gly Gly Trp Thr Trp
            100                 105                 110

Ser Gly Gly Phe Thr Asp Ala Val Lys Asn Pro Ala Ala Phe Ala Lys
        115                 120                 125

Ser Cys His Asp Leu Val Glu Asp Pro Arg Trp Ala Asp Val Phe Asp
    130                 135                 140

Gly Ile Asp Leu Asp Trp Glu Tyr Pro Asn Ala Cys Gly Leu Ser Cys
145                 150                 155                 160

Asp Ser Ser Gly Pro Ala Ala Leu Lys Asn Met Val Gln Ala Met Arg
                165                 170                 175

Ala Gln Phe Gly Thr Asp Leu Val Thr Ala Ala Ile Thr Ala Asp Ala
            180                 185                 190

Ser Ser Gly Gly Lys Leu Asp Ala Ala Asp Tyr Ala Gly Ala Ala Gln
        195                 200                 205

Tyr Phe Asp Trp Tyr Asn Val Met Thr Tyr Asp Phe Phe Gly Ala Trp
    210                 215                 220

Asp Lys Thr Gly Pro Thr Ala Pro His Ser Ala Leu Asn Ser Tyr Ser
225                 230                 235                 240

Gly Ile Pro Lys Ala Asp Phe His Ser Ala Ala Ile Ala Lys Leu
                245                 250                 255

Lys Ala Lys Gly Val Pro Ala Ser Lys Leu Leu Gly Ile Gly Phe
            260                 265                 270

Tyr Gly Arg Gly Trp Thr Gly Val Thr Gln Asp Ala Pro Gly Gly Thr
        275                 280                 285

Ala Thr Gly Pro Ala Thr Gly Thr Tyr Glu Ala Gly Ile Glu Asp Tyr
    290                 295                 300

Lys Val Leu Lys Asn Thr Cys Pro Ala Thr Gly Thr Val Gly Gly Thr
305                 310                 315                 320

Ala Tyr Ala Lys Cys Gly Ser Asn Trp Trp Ser Tyr Asp Thr Pro Ala
                325                 330                 335
```

```
Thr Ile Lys Thr Lys Met Thr Trp Ala Lys Asp Gln Gly Leu Gly Gly
            340                 345                 350

Ala Phe Phe Trp Glu Phe Ser Gly Asp Thr Ala Gly Gly Glu Leu Val
        355                 360                 365

Ser Ala Met Asp Ser Gly Leu Arg
        370             375

(2) INFORMATION FOR SEQ ID NO:4:

(i) SEQUENCE CHARACTERISTICS:
          (A) LENGTH: 2712 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:4:
```

| | | | | | |
|---|---|---|---|---|---|
| GTCGACTGGT | ACAACGTGAT | GACCTACGAC | TACTTCGGCA | CCTGGGCCGC | CCAGGGCCCG | 60
| ACGGCGCCCC | ACTCGCCGCT | CACCGCCTAC | CCGGGCATCC | AGGGCGAGCA | CAACACCTCC | 120
| TCGGCCACCA | TCGCCAAGCT | GCGGGGCAAG | GGCATCCCGG | CGAAGAAGCT | GCTGCTGGGC | 180
| ATCGGCGCCT | ACGCCGCGG | CTGGACCGGC | GTCACCCAGG | ACGCCCCGG | CGGCACCGCC | 240
| ACCGGCCCGG | CCGCCGGCAC | CTACGAGGCG | GGCAACGAGG | AGTACCGGGT | GCTGGCCGAG | 300
| AAGTGCCCGG | CCACCGGCAC | CGCCGGCGGC | ACCGCGTACG | CCAAGTGCGG | CGACGACTGG | 360
| TGGAGTTACG | ACACCCCTGA | GACGGTGACG | GGCAAGATGG | CCTGGGCGAA | GAAGCAGAAG | 420
| CTCGGCGGTG | CCTTCCTCTG | GGAGTTCGCC | GGCGACGGCG | CCAAGGGCGA | TCTGTTCAGG | 480
| GCGATGCACG | AGGGGCTGCG | CTGACCGGCC | GGGCACTCAC | CCGGAACTGA | CCCTTCCCGC | 540
| ACGGCCGTCC | GCCGTGGCAC | CGGAGCTCCG | GTCGCCGCGG | CGGGCGGCCG | TGTCCGCATG | 600
| TCGCCACCCC | CGCGCACCAG | GCGCGATCCG | GCCGAACTTT | CCTTTGGTCC | AGACCTCTTG | 660
| ACCTCTGGTC | CAGACCTTTT | CTACTCTCGC | CCCACTGCGG | TGGGCACATC | GGTCGTCGGT | 720
| GCTCACGGGC | GTCGCAGGGT | TCCGCCCCCA | TACGTCCGGA | CCTCTTGAGG | AGTACGCCTT | 780
| GAGTACGGTT | TCCCCCAGCA | CCGACGGCGC | CCGCAGCCGT | CCCAGACCCC | TCAGCCGCTT | 840
| CCGCCGGCGC | GCGCTGGCCG | CGCTCGTCGG | CCTCGCGGTC | CCCTTCGCCG | GGATGGTCGG | 900
| CCTCGCCGCC | CCCACCCAGG | CCGCCGAGGC | CGCGGCCGAC | CCCAGCGCCT | CCTACACCAG | 960
| GACGCAGGAC | TGGGGCAGCG | GCTTCGAGGG | CAAGTGGACG | GTGAAGAACA | CCGGCACCGC | 1020
| CCCCCTCAGC | GGCTGGACCC | TGGAGTGGGA | CTTCCCCGCC | GGAACCAAGG | TGACCTCGGC | 1080
| CTGGGACGCC | GACGTCACCA | ACAACGGCGA | CCACTGGACC | GCCAAGAACA | AGAGCTGGGC | 1140
| GGGGAGCCTC | GCCCCCGGCG | CCTCGGTCAG | CTTCGGCTTC | AACGGCACCG | GCCCCGGCAC | 1200
| CCCCTCGGGC | TGCAAGCTCA | ACGGCGCCTC | CTGCGACGGC | GGCAGCGTCC | CCGGCGACAC | 1260
| CCCGCCCACC | GCCCCCGGCA | CCCCCACCGC | CAGTGACCTC | ACCAAGAACT | CGGTGAAGCT | 1320
| CTCCTGGAAG | GCGGCCACCG | ACGACAAGGG | CGTCAAGAAC | TACGACGTCC | TGCGCGACGG | 1380
| CGCCAAGGTC | GCCACCGTCA | CCGCCACCAC | CTTCACCGAC | CAGAACCTCG | CCCCCGGCAC | 1440
| CGACTACTCC | TACTCGGTCC | AGGCCCGCGA | CACCGCCGAC | CAGACCGGCC | CGGTCAGCGC | 1500
| CCCCGTCAAG | GTCACCACCC | CCGGCGACGG | CACGGGCCCC | GGCCCCGGCC | CCGCGAGAA | 1560
| GATCAACCTC | GGCTACTTCA | CCGAGTGGGG | CGTCTACGGC | CGCAACTACC | ACGTCAAAAA | 1620
| CCTGGTGACC | TCCGGCTCCG | CCGAGAAGAT | CACCCACATC | AACTACTCCT | TCGGCAACGT | 1680

-continued

| | | | | |
|---|---|---|---|---|
| CCAGGGCGGC | AAGTGCACCA | TCGGTGACAG | CTTCGCCGCC | TACGACAAGG CGTACACCGC 1740 |
| CGCCGAGTCG | GTCGACGGCG | TCGCCGACAC | CTGGGACCAG | CCGCTGCGCG GCAACTTCAA 1800 |
| CCAGCTCCGC | AAGCTCAAGG | CCAAGTACCC | GCACATCAAG | GTCCTCTGGT CCTTCGGCGG 1860 |
| CTGGACCTGG | TCCGGCGGCT | TCACCGACGC | CGTGAAGAAC | CCGGCCGCCT TCGCCAAGTC 1920 |
| CTGCCACGAC | CTGGTCGAGG | ACCCGCGCTG | GGCCGACGTC | TTCGACGGCA TCGACCTCGA 1980 |
| CTGGGAGTAC | CCGAACGCCT | GCGGCCTCAG | CTGCGACAGC | TCCGGTCCGG CCGCGCTGAA 2040 |
| GAACATGGTC | CAGGCGATGC | GCGCCCAGTT | CGGCACCGAC | CTGGTCACCG CCGCCATCAC 2100 |
| CGCCGACGCC | AGCTCCGGCG | GCAAGCTCGA | CGCCGCCGAC | TACGCGGGCG CCGCCCAGTA 2160 |
| CTTCGACTGG | TACAACGTGA | TGACGTACGA | CTTCTTCGGC | GCCTGGGACA AGACCGGCCC 2220 |
| GACCGCGCCC | CACTCGGCCC | TGAACTCCTA | CAGCGGCATC | CCCAAGGCCG ACTTCCACTC 2280 |
| GGCCGCCGCC | ATCGCCAAGC | TCAAGGCGAA | GGGCGTCCCG | GCGAGCAAGC TCCTGCTCGG 2340 |
| CATCGGCTTC | TACGGCCGCG | GCTGGACCGG | CGTCACCCAG | GACGCCCCGG GCGGCACCGC 2400 |
| CACCGGCCCG | GCCACCGGCA | CCTACGAGGC | GGGCATCGAG | GACTACAAGG TCCTCAAGAA 2460 |
| CACCTGCCCC | GCCACCGGCA | CCGTCGGCGG | CACCGCGTAC | GCCAAGTGCG GCAGCAACTG 2520 |
| GTGGAGCTAC | GACACCCCGG | CCACCATCAA | GACCAAGATG | ACCTGGGCCA AGGACCAGGG 2580 |
| CCTCGGCGGC | GCCTTCTTCT | GGGAGTTCAG | CGGTGACACC | GCGGGCGGCG AACTGGTCTC 2640 |
| CGCGATGGAC | TCCGGCCTCC | GCTAGCCCCG | GACCGGCACC | CCGCCCGAAC CACTAGCACG 2700 |
| ACCTCCCCCG | GA | | | 2712 |